US005614183A

United States Patent [19]
Ralph et al.

[11] Patent Number: 5,614,183
[45] Date of Patent: Mar. 25, 1997

[54] USE OF CSF-1 TO TREAT BACTERIAL INFECTIONS

[75] Inventors: Peter Ralph, Orinda; Kong T. Chong, Union City, both of Calif.

[73] Assignee: Chiron Corporation, Emeryville, Calif.

[21] Appl. No.: 371,803

[22] Filed: Jan. 11, 1995

Related U.S. Application Data

[62] Division of Ser. No. 220,454, Mar. 31, 1994, Pat. No. 5,556,620, which is a continuation of Ser. No. 24,094, Feb. 26, 1993, abandoned, which is a continuation of Ser. No. 505,256, Apr. 5, 1990, abandoned, which is a continuation-in-part of Ser. No. 243,253, Sep. 14, 1988, abandoned, which is a continuation-in-part of Ser. No. 99,872, Sep. 22, 1987, Pat. No. 5,104,650, which is a continuation-in-part of Ser. No. 876,819, Jun. 20, 1986, abandoned, which is a continuation-in-part of Ser. No. 821,068, Jan. 21, 1986, abandoned, which is a continuation-in-part of Ser. No. 756,814, Jul. 18, 1985, abandoned, which is a continuation-in-part of Ser. No. 744,924, Jun. 14, 1985, abandoned, which is a continuation-in-part of Ser. No. 728,834, Apr. 30, 1985, abandoned, which is a continuation-in-part of Ser. No. 698,359, Feb. 5, 1985, abandoned.

[51] Int. Cl.$^6$ .............................. A61K 38/19; C07K 14/53
[52] U.S. Cl. ................... 424/85.1; 424/278.1; 514/2; 514/8; 514/12; 514/885
[58] Field of Search .................... 424/85.1, 278.1; 514/2, 8, 12, 885

[56] References Cited

U.S. PATENT DOCUMENTS

| | | | |
|---|---|---|---|
| 4,230,697 | 10/1980 | Nishida et al. | 424/177 |
| 4,275,056 | 6/1981 | Takaku et al. | 424/101 |
| 4,342,828 | 8/1982 | Takaku et al. | 435/41 |
| 4,482,485 | 12/1984 | Funakoshi et al. | 530/397 |
| 4,518,584 | 5/1985 | Mark et al. | 424/85 |
| 4,690,915 | 9/1987 | Rosenberg | 514/2 |
| 4,808,611 | 2/1989 | Cosman | 514/12 |
| 4,833,127 | 8/1989 | Ono | 514/21 |
| 4,847,201 | 7/1989 | Kaswasaki et al. | 435/69.5 |
| 4,847,325 | 7/1989 | Shadle et al. | 525/54 |
| 4,868,119 | 9/1989 | Clark et al. | 435/240.2 |
| 4,879,227 | 11/1989 | Clark | 435/172.3 |

FOREIGN PATENT DOCUMENTS

| | | |
|---|---|---|
| 0118915 | 9/1984 | European Pat. Off. |
| 0211684 | 2/1987 | European Pat. Off. |
| 0261592 | 3/1988 | European Pat. Off. |
| 0272779 | 6/1988 | European Pat. Off. |
| 0273778 | 7/1988 | European Pat. Off. |
| 0276551 | 8/1988 | European Pat. Off. |
| 8604607 | 8/1986 | WIPO. |
| 8604587 | 8/1986 | WIPO. |
| 8702060 | 4/1987 | WIPO. |
| 8703204 | 6/1987 | WIPO. |
| 8706954 | 11/1987 | WIPO. |
| 8805786 | 8/1988 | WIPO. |
| 8806452 | 9/1988 | WIPO. |
| 8902746 | 4/1989 | WIPO. |
| 8903687 | 5/1989 | WIPO. |
| 8905656 | 6/1989 | WIPO. |

OTHER PUBLICATIONS

Gorgen et al. (1992) J. of Immunol. vol. 149, No. 3, pp. 918–924.
Van Brunt, Biotechnol vol. 7, Jan. 1986, pp. 15–16.
ten Dijke et al, Biotechnol vol. 7, Aug. 1989, pp. 793–798.
Schultz et al, J. Cell. Biochem, Supplemental 15F, 1991, p. 164 (abstract #QO25).
Luger et al, J. Am. Acad. Dermatol, 1991, vol. 24, pp. 15–26.
Kalter et al., J. of Immunol. (1991) 146:298–306.
Kunder et al., Anti. Res. (1993) 21:233–245.
Lloret et al., Arch. of Med. Res. (1992) 23:139–141.
Ralph et al., J. of Immunol. (1982) 129:427–432.
Munn et al., Blood (1988) 72:127a.
Bajorin et al., Proc. of ASCO (1990) 9:183.
Blum et al., Proc. of ASCO (1993) 12:474.
Motoyoshi, Oncology (1994) 51:198–204.
Miller et al., Proc. of ASCO (1990) 31:242.
Falk et al., J. of Leukocyte Biol. (1988) 43:471–476.
Suzu et al., Cancer Res. (1989) 49:5913–17.
Curley et al., Lymphokine Res. (1990) 9:355–363.
Thomassen et al., J. of Biolog. Response Modif. (1990) 9:87–91.
Butler, Oncology & Biotech News (1990) 1.
Hume et al., Immunol. Cell Biol. (1989) 67:243–249.
Ralph et al., Hemat. Growth Factors in Trans. Med. (1990) pp. 43–63.
Khwaja et al., British J. of Haemat. (1991) 77:25–31.
Komiyama et al., Blood (1988) 71:41–45.
Masaoka et al., Bone Marrow Trans. (1988) 3:121–127.
Hume et al., J. of Cellular Biochem. (1988) 38:127–138.
Broxmeyer et al., J. of Immunol. (1988) 141:3405–09.
Metcalf et al., Immunol. Cell Biol. (1987) 65:35–43.
Suzu et al., Jpn. J. Cancer Res. (1990) 81:79–84.
Adachi, T. et al., Cancer Immunol. Immunother (1993) 37:1–6.
Brugger, W. et al., Acta Haematol (1991) 86:138–147.
Bukowski, R.M. et al., J. of Clin. Oncology (1994) 12:97–106.
Cole, D.J. et al., J. of Nat'l Cancer Institute (1994) 86:39–51.
Dale, D., Clinical Infectious Diseases (1994) Supp2:S180–S188.
Denis, M., Clin. Exp. Immunol. (1991) 84:200–206.
Denis, M., J. of Leukocyte Biology (1991) 50:296–302.

(List continued on next page.)

Primary Examiner—John Ulm
Assistant Examiner—Prema Mertz
Attorney, Agent, or Firm—Philip L. McGarrigle, Jr.; Robert P. Blackburn

[57] ABSTRACT

A colony stimulating factor, CSF-1, is a lymphokine useful in treating or preventing bacterial, viral or fungal infections, neoplasms, leukopenia, wounds, and in overcoming the immunosuppression induced by chemotherapy or resulting from other causes. CSF-1 is obtained in usable amounts by recombinant methods, including cloning and expression of the murine and human DNA sequences encoding this protein.

4 Claims, 6 Drawing Sheets

OTHER PUBLICATIONS

Douzono, M. et al., *Exp. Hematology* (1992) 20:245.
Doyle, A. et al., *Infect. & Immun.* (1992) 60:1465–72.
Hume, D. et al., *Lymphokine Research* (1989) 8:69–77.
Kayashima, S. et al., *Infect. & Immun.* (1991) 59:4677–80.
Kunze, G. et al., *J. Basic Microbiol.* (1985) 25(2):141–144.
Langermans, J. et al., *Biotherapy* (1994) 7:169–178.
Lu, L. et al., *Exp. Hematol.* (1991) 19:804–809.
Lu, L. et al., *Int. J. Cancer* (1991) 47:143–147.
Mitraki, A. et al., *Bio/Technology* (1989) 7:690–697.
Morstyn, G. et al., *Cancer Research* (1988) 48:5624–5637.
Murray, H., *Clinical Infectious Diseases* (1993) 17(Suppl2):S407–13.
Petros W. et al., *Exper. Hematology* (1994) 22:582–586.
Redman B.G. et al., *J. of Immunotherapy* (1992) 12:50–54.
Roilides E. et al., *Clinical Infectious Diseases* (1992) 15:508–524.
Roilides E. et al., *Hematology/Oncology Clinics of North America* (1993) 7:841–864.
Sanda M. et al., *J. of Clinical Oncology* (1992) 10:1643–49.
Shiratsuchi H. et al., *J. of Immunol.* (1991) 146:3165–3170.
Tsakona C.P., et al., *Bone Marrow Transplantation* (1993) 11:433–436.
Tsukada H. et al., *Amer. J. of Hematology* (1994) 45:325–329.
VandePol C.J. et al., *Biotechnology Therapeutics* (1991) 2:231–239.
Weiner L.M. et al., *Cancer Research* (1994) 54:4084–4090.
Bock, S. et al., *Cancer Research* (1991) 51:2649–54.
Kitano et al., *British J. of Research* (1993) 85:176–178.
Yanai N. et al., *Jpn. J. Cancer Res.* (1990 81:355–362.
Tsakona et al., *Clin. Lab. Haemat.* (1992) 14:273–280.
Warren and Ralph, *J. Immunol.*, 137:–281–2285 (1986).
Ralph et al., *Immunobiol.* 172:194–204 (1986).
Ralph et al., *Cell Immunol.* 76:10–21 (1983).
Ralph et al., *Cell Immunol.* 105:270–278 (1987).
Lee et al., *J. Immunol.* 138:3019–3022 (1987).
Metcalf, D., *Immunol. Cell Biol.* 65:35–43, Feb. 1987, (abstract enclosed).
Broxmeyer et al., *Blood Cells* 13:31–48 (1987) (abstract enclosed).
Bagby, *Blood Cells* 13:147–159 (1987 (abstract enclosed).
Adachi et al., *Horumon to Rinsho* 35(5):555–562 (1987) (abstract enclosed).
Tauber and Tauber, *Nucl. Med. Biol.* 14:407–419 (1987) (abstract enclosed).
Metcalf, *Proc. R. Soc.* London 230:389–423 (1987).
Hanamura et al., *Leukemia* 1:497–503 (1987) (abstract enclosed).
Vadas et al., *Immunol. Cell Biol.* 65:141–145 (1987) (abstract enclosed).
Metcalf, *Immunol. Cell Biol.* 65:35–43 (1987) (abstract enclosed).
Takaku, *Pharma. Med.* 5:27–31 (1987) (abstract enclosed).
Ralph et al., *Cold Spring Harbor Symp. Quant. Biol.* 51:679–683 (1986) (abstract enclosed).
Dayer, *Med. Hyg.* 45:1246–1248 (1987) (abstract enclosed).
Sieff, *J. Clin. Invest.* 79:1449–1457 (1987) (abstract enclosed).
Kawakita, *Jikken Igaku* 4:912–914 (1986).
Hume et al., *Lympholine Res.* 6:127–139 (1987) (abstract enclosed).
Platzer et al., *Blut* 54:129–136 (1987) (abstract enclosed).

Gough, *Oncog. Growth Control*, 35–42, ed. by Kahn and Graf. Springer:Berlin, Fed. Republic Ger. (1986) (abstract enclosed).
Asano, *Jikken Igaker* 4:908–911 (1986) (abstract enclosed).
Galelli, A. et al., *Infect. Immun.* 46:495–500 (1984).
Hibbs, 1974, Science, 184:468–471.
Fidler, et al., 1981, Lymphokines, 3:345–363.
Fidler, 1975, J. of the National Cancer Institute, 55, 1159–1163.
Kleinerman, et al., 1983, Cancer Research, 43:2010–2014.
Marino et al., 1982, J. of Immunology, 128:2816–2823.
Kleinerman et al., 1983, J. of Clin. Invest., 72:304–315.
Cameron et al., 1979, J. Clin. Invest., 63:977–984.
Bucana et al., 1983, AJP, 112:101–111.
Churchill et al., 1975, J. of Immunology, 115:781–786.
Kleinerman et al., 1983, Lymphokine Research, 2:7–12.
Key, et al., 1982, Adv. Exp. Med. Biol., 146:265–314.
DeMaeyer, E., 1988, Interferons and Other Regulatory Cytokines, Wiley & Sons, Inc., Chpt. 10, pp. 195–220.
Paul, W.E., 1984, Fundamental Immunology, pp. 102–103.
Roitt, I. M., 1988, Essential Immunology, Sixth Edition, Chpt. 13, pp. 232–233, 236.
Sone, S., et al., 1986, Cancer Immunol Immunother, 21:93–99.
Erickson, K.L., et al., 1982, Cellular Immunology, 72:195–201.
Kleinerman, E.S., et al., 1984, Cancer Research, 44:4470–4475.
Arden–Jones, M.P., et al., 1988, Cellular Immunology, 113:361–375.
DeMaeyer, E., et al., 1988, Interferons and Other Regulatory Cytokines, Chpt. 8, pp. 154–173.
Stewart, W.E., II, 1979, The Interferon System, pp. 200–206, 224–231, 292–293, 309–310.
Higuchi, M., et al., 1990, The Journal of Immunology, 144:1425–1431.
Kern, D.E., et al., 1989, The Journal of Immunology, 143:4308–4316.
Saito, T., et al., 1987, Cancer Research, 47:673–679.
Ho, M., 1987, Ann. Rev. Med., 38:51–59.
Fidler, I.J., et al., 1985, The Journal of Immunology, 135(6):4289–4296.
Rosenberg, 1984, Science, 223:1412.
Dexter, 1984, *Nature* 309:746–747.
Vadas et al., 1983, *J. Immunol.* 130:795–799.
Clark, 1987, *Science* 236:1229–1237.
Sachs, 1987, *Science* 238:1374–1379.
Das et al., 1981, *Blood* 58:630–641.
Gough et al., 1984, *Nature* 309:763–767.
Fung et al., 1984, *Nature* 307:233–237.
Yokota et al., 1984, *Proc. Natl. Acad. Sci. USA* 81:1070–1074.
Wong et al., 1985, *Science* 228:810–185.
Lee et al., 1985, *Proc. Natl. Acad. Sci. USA* 82:4360–4364.
Cantrell et al., 1985, *Proc. Natl. Acad. Sci. USA* 82:6250–6254.
Ralph et al., 1986, *Immunobiol.* 172:194–204.
Ralph et al., 1983, *Cell. Immunol.* 76:10–21.
Ralph et al., 1987, *Cell. Immunol.* 105:270–279.
Warren et al., 1986, *J. Immunol.* 137:2281–2285.
Lee et al., 1987, *J. Immunol.* 138:3019–3022.
Metcalf, 1970, *J. Cell. Physiol.* 76:89–100.
Moore et al., 1984, *Science* 223:178–181.
Stanley, 1981, *The Lymphokines*, Stewart, II et al., ed. Humana Press, Clifton, NJ, pp. 101–132.

Byrne et al., 1981, *Cell. Biol.* 91:848–853.
Fleit et al., 1981, *J. Cell. Physiol.* 108:347–352.
Wing et al., 1982, *J. Clin. Invest.* 69:270–276.
Nogawa et al., 1980, *Cell. Immunol.* 53:116–124.
Ladner et al., 1987, *Embo. J.* 6:(9):2693–2698.
Stanley, 1985, *Methods Enzymol.* 116:564–587.
Csejtey et al., 1986, *Biochem. Biophys. Res. Comm.* 138:238–245.
Moore et al., 1983, *J. Immunol.* 131:2374–2378.
Prystowsky et al., 1984, *Am. J. Pathol.* 114:149–156.
Stanley et al., 1972, *J. Lab. Clin. Med.* 79:657–668.
Stanley et al., 1981, *J. Immunol. Meth.* 42:253–284.
Wang et al., 1983, *J. Cell. Biochem.* 21:263–275.
Hunkapiller et al., 1984, *Science* 226:304–311.
Payvar et al., 1979, *J. Biol. Chem.* 254:7636–7642.
Colotta et al., 1984, *J. Immunol.* 132:936–944.
Goodson and Hunt, 1982, *J. Surg. Res.* 33:394–401.
Eisenger et al., 1988, *Proc. Natl. Acad. Sci. USA* 85:1937–1941.
Fotev et al., 1987, *J. Pathol.* 151:209–219.
Ishizaka et al., 1986, *Exp. Hematol* 14:1–8.
Motoyoshi et al., 1978, *Blood* 52:1012–1020.
Motoyoshi et al., 1983, *Blood* 62(3):685–688.
Warren et al., 1985, *J. Immunol.* 134(2):982–989.
Metcalf, 1986, *Blood* 67(2):257–267.
Das et al., 1982, *J. Biol. Chem.* 257:13679–13681.
Becker et al., 1987, *J. Immunol.* 139:3703–3709.
Metcalf, 1987, *Immunol. Cell. Biol.* 65:35–43.
Metcalf, 1985, *Science* 229:16–22.
Sieff, 1987, *J. Clin. Invest.* 79: 1549–1557.
Koren et al., 1986, *J. Biol. Response Modif.* 5(5):481–489 also see Chem. Ab. #18915sb).
Koren et al., 1986, *J. Biol. Response Modif.* 5(6):571–580 (also see Chem. Ab. #82827u).
Motoyoshi et al., 1986, *Immunobiol.* 172:205–212.
Motoyoshi et al., 1986, *Exp. Hematol.* 14:1069–1075.
Bartocci et al., 1986, *J. Exp. Med.* 164:956–961.
Masaoka et al., 1988, *Exp. Hematol.* 16(6):469.
Chong et al., 1988, *FASEB J.* 2:A1474.
Karbassi et al., 1987, *J. Immunol.* 139:417–421.
Tsuneoka et al., 1984, *Cell Structure & Function* 9:67–81.
Metcalf et al., 1985, *Leukemia Res.* 9:35–50.
Kanada et al., 1987, *J. Pharmacobio-Dyn.* 10:215–219.
Wing et al., 1986, *J. Immunol.* 137:2768–2773.
Sampson–Johannes et al., 1988, *J. Immunol.* 114:3680–3686.
Nakoinz et al., 1988, *Cell. Immunol.* 116:331–340.
Wang et al., 1988, *J. Immunol.* 141:575–579.
Motoyoshi et al., 1982, *Blood* 60:1378–1386.
Gendleman et al., 1988, *J. Exp. Med.* 167:1428–1441.
Ralph, et al., 1986, *Blood* 68:633–639.
Moore et al., *Recent Advances in Leukemia & Lymphoma* Alan R. Liss, Inc., pp. 445–456.
Mochizuki et al., *Proc. Natl. Acad. Sci. USA* 84:5267–5271.
Zsebo et al., 1988, *Blood* 71:962–968.
Lyberg et al., 1987, *J. Cell. Physiol.* 132:367–376.
Takahashi et al., 1988, *Bioch. Biophy. Res. Comm.* 152:1401–1409.
Sakai et al., 1987, *FEBS. Lett.* 222:341–344.
Strassmann et al., 1988, *J. Immunol.* 140:2645–2651.
Tao et al., 1987, *Biol. Chem. Hoppe–Sayler* 368:187–194.
Ralph et al., 1989, *Macrophage–Derived Cell Regulatory Factors. Cytokines.* vol. 1, C. Sorg, ed. Karger:Basel, pp. 1–18.
Ralph, 1989, *Human Monocytes* Asherson et al., eds., Academic Press pp. 227–246.
Shadle et al., 1989, *J. Cell. Biochem.* 40:91–107.
Bern et al., *Biotechnology* vol. 3, 1985, pp. 51–53.
Stanley et al., (1977) *J. Biol Chem* 252:4305.
Wong et al., (1987) *Science* 235:1504.
Kawasaki et al., (1985) *Science* 230:291.
Cerretti et al., (1988) *Molecular Immunol* 25:761–770.
Unkeless et al., (1988) *Ann Rev Immun* 6:251–281.
Hunt et al., (1984) *Surgery* 96:48–54.
Cheers et al., (1989) *Infect and Immun* 57:1512–1516.
Wang et al., (1989) *J Immunol* 143:671–677.
Nozawa et al., (1980) *Cell Immunol* 53:116–124.
Mufson et al., (1989) *Cell Immunol* 119:182–192.
Munn et al., (1989) *J Exp Med* 170:511–526.
Orgill et al., (1988) *Crit Care Med* 16:899–908.
Browder et al., (1988) *Surgery* 104:224–230.
Becker et al., (1987) *J Immunol* 139:3703–3709.
Motoyoshi et al., (1982) *Blood* 60:1378–1386.
Hatake et al., (1985) *J Chromatography* 344:339–344.
Metcalf, (1985) *Science* 229:16–22.

USE OF CSF-1 TO TREAT BACTERIAL INFECTIONS

CROSS-REFERENCE TO RELATED APPLICATION

This application is a divisional of U.S. patent application Ser. No. 08/220,454, filed Mar. 31, 1994, now U.S. Pat. No. 5,556,620, which is a continuation of U.S. patent application Ser. No. 08/024,094, filed Feb. 26, 1993 (now bandoned), which is a continuation of U.S. patent application Ser. No. 07/505,256, filed Apr. 5, 1990 (now abandoned), which is a continuation-in-part of U.S. patent application Ser. No. 243,253, filed September 1988 (now abandoned), which is a continuation-in-part of U.S. patent application Ser. No. 07/099,872, filed 22 Sep. 1987 (now U.S. Pat. No. 5,104, 650), which is a continuation-in-part of U.S. patent application Ser. No. 06/876,819, filed 20 Jun. 1986 (which was refiled as U.S. patent application Ser. No. 157,094, filed 2 Feb. 1988 and. issued as U.S. Pat. No. 4,847,201 (now abandoned)), which is a continuation-in-part of U.S. patent application Ser. No. 06/821,068, filed 21 Jan. 1986 (now abandoned), which is a continuation-in-part of U.S. patent application Ser. No. 06/756,814, filed 18 Jul. 1985 (now abandoned), which is a continuation-in-part of U.S. patent Application Ser. No. 06/744,924, filed 14 Jun 1985 (now abandoned), which is a continuation-in-part of U.S. patent application Ser. No. 06/728,834, filed 30 Apr. 1985 (now abandoned), which is a continuation-in-part of U.S. Ser. No. 06/698,359, filed 5 Feb. 1985 (now abandoned).

TECHNICAL FIELD

The present invention relates to the various therapeutic uses of recombinantly produced human colony stimulating factor-1 (CSF-1).

BACKGROUND

The ability of certain factors produced in very low concentration in a variety of tissues to stimulate the growth and development of bone marrow progenitor cells into macrophages and/or granulocytes has been known for nearly 15 years. The presence of such factors in sera, urine samples, and tissue extracts from a number of species is demonstrable using an in vitro assay which measures the stimulation of colony formation by bone marrow cells plated in semi-solid culture medium. There are no acceptable in vivo assays. Because these factors induce the formation of such colonies, the factors collectively have been called Colony Stimulating Factors (CSF).

More recently, it has been shown that there are at least four subclasses of human CSF proteins which can be defined according to the types of cells found in the resultant colonies. One subclass, CSF-1, results in colonies containing predominantly macrophages. Other subclasses produce colonies which contain both neutrophilic granulocytes and macrophages (GM-CSF); which contain predominantly neutrophilic granulocytes (G-CSF); and which contain neutrophilic and eosinophilic granulocytes, macrophages, and other myeloid cell types (basophils, erythrocytes, and megokaryocytes) (IL-3).

GM-CSF is described by Gough, et al, *Nature* (1984) 309:763–767. This protein is further described in W087/02060, published 9 Apr. 1987 as being useful to treat cancer patients to regenerate leukocytes after traditional cancer treatment, and to reduce the likelihood of viral, bacterial, fungal and parasitic infection, such as acquired immune deficiency syndrome (AIDS). Human IL-3 has been cloned by Yank, Y. C., et al, *Cell* (1986) 47:3.

There are murine factors analogous to the above human CSFs, including a murine factor called IL-3 which induces colonies from murine bone marrow cells which contain all these cell types plus megakaryocytes, erythrocytes, and mast cells, in various combinations. Murine IL-3 has been cloned by Fung, M. C., et al, *Nature* (1984) 307:233. See also Yokota, T., et al, *Proc Natl Acad Sci (USA)* (1984) 81:1070–1074; Wong, G. G., et al, *Science* (1985) 228:810–815; Lee, F., et al, *Proc. Natl Acad Sci (USA)* (1985) 82:4360–4364; and Canttell, M. A., et al, *Proc Natl Acad Sci (USA)* (1985) 82:6250–6254.). These CSFs and others have been reviewed by Dexter, T. M., *Nature* (1984) 309:746, and Vadas, M. A., et al, J Immunol (1983) 130:793, Clark, S. C., *Science* (1987) 236:1229, and Sachs, L., Science (1987) 238:1374.

The cloning and expression of G-CSF is described in U.S. Pat. No. 4,810,643 and a method to purify G-CSF from human oral cancer tissue is described in U.S. Pat. No. 4,833,127.

The invention herein is concerned with the recombinant production of proteins which are members of the first of these subclasses, CSF-1. This subclass has been further characterized and delineated by specific radioimmunoassays and radioreceptor assays—e.g., antibodies raised against purified CSF-1 are able to suppress specifically CSF-1 activity, without affecting the biological activities of the other subclasses, and macrophage cell line J774 contains receptors which bind CSF-1 specifically. A description of these assays was published by Das, S. K., et al, Blood (1981) 58:630.

A significant difficulty in putting CSF proteins in general, and CSF-1 in particular, to any useful function has been their unavailability in distinct and characterizable form in sufficient amounts to make their employment in therapeutic use practical or even possible. The present invention remedies these deficiencies by providing purified human and murine CSF-1 in useful amounts through recombinant techniques and discloses various therapeutic uses thereof.

Treatment of patients suffering from AIDS with CSF-1, alone or together with erythropoietin and/or an antiviral agent and/or IL-2 is reported in W087/03204, published 4 Jun. 1987. U.S. Pat. No. 4,482,485, issued 13 Nov. 1984 states that CSF isolated from human urine can be used for a supporting role in the treatment of cancer. In addition, EP 118,915, published 19 Sep. 1984 reports production of CSF for preventing and treating granulocytopenia and macrophagocytopenia in patients receiving cancer therapy, for preventing infections, and for treating patients with implanted bone marrow.

In addition, CSF-1 is reported to stimulate nonspecific tumoricidal activity (Ralph et al, *Immunobiol* (1986) 172:194–204). Ralph et al, *Cell Immunol* (1983) 76:10–21 reported that CSF-1 has no immediate direct role in activation of macrophages for tumoricidal and microbiocidal activities against fibrosarcoma 1023, lymphoma 18-8, and *L. tropica* amastigotes. Ralph et al, *Cell Immunol* (1987) 105:270–279 reports the delayed tumoricidal effect of CSF-1 alone and the added tumoricidal effect of a combination of CSF-1 and lymphokine on murine sarcoma TU5 targets. Copending, commonly owned U.S. application Ser. No. 126,221, filed 19 Feb. 1988, discloses the synergistic effect of CSF-1 and G-CSF to stimulate the immune system.

In addition, Warren et al, *J Immunol* (1986) 137:2281–2285 discloses that CSF-1 stimulates monocyte production of interferon, TNF and colony stimulating activity. Lee et al, *J Immunol* (1987) 138:3019–3022 discloses CSF-1-induced resistance to viral infection in murine macrophages.

SUMMARY OF THE INVENTION

In one aspect of the invention, therapeutic treatments based on the ability of CSF-1 to induce resistance to a number of infectious diseases in mammals, including those caused by bacterial, viral or fungal agents, are disclosed. Yet a further aspect concerns the ability of CSF-1 to promote the repair of tissue damage for use in wound healing. Lastly, the invention provides methods of treating tumor cells in mammals by using an effective amount of CSF-1 to treat tumor burden. In one aspect of this indication, the invention relates to methods of enhancing the stimulation of antibody-dependent targeted cellular cytotoxicity using human effector cells, such as, bone marrow derived cells, tissue macrophages, or peripheral blood mononuclear cells against tumor cells, all of which are mediated by a bifunctional antibody. In addition, the invention relates to pharmaceutical compositions comprising CSF-1 or a mixture thereof with a cytokine, lymphokine, or with an excipient for use in the various aforementioned indications.

BEST MODES FOR CARRYING OUT THE INVENTION

A. Definitions

Figure 1:
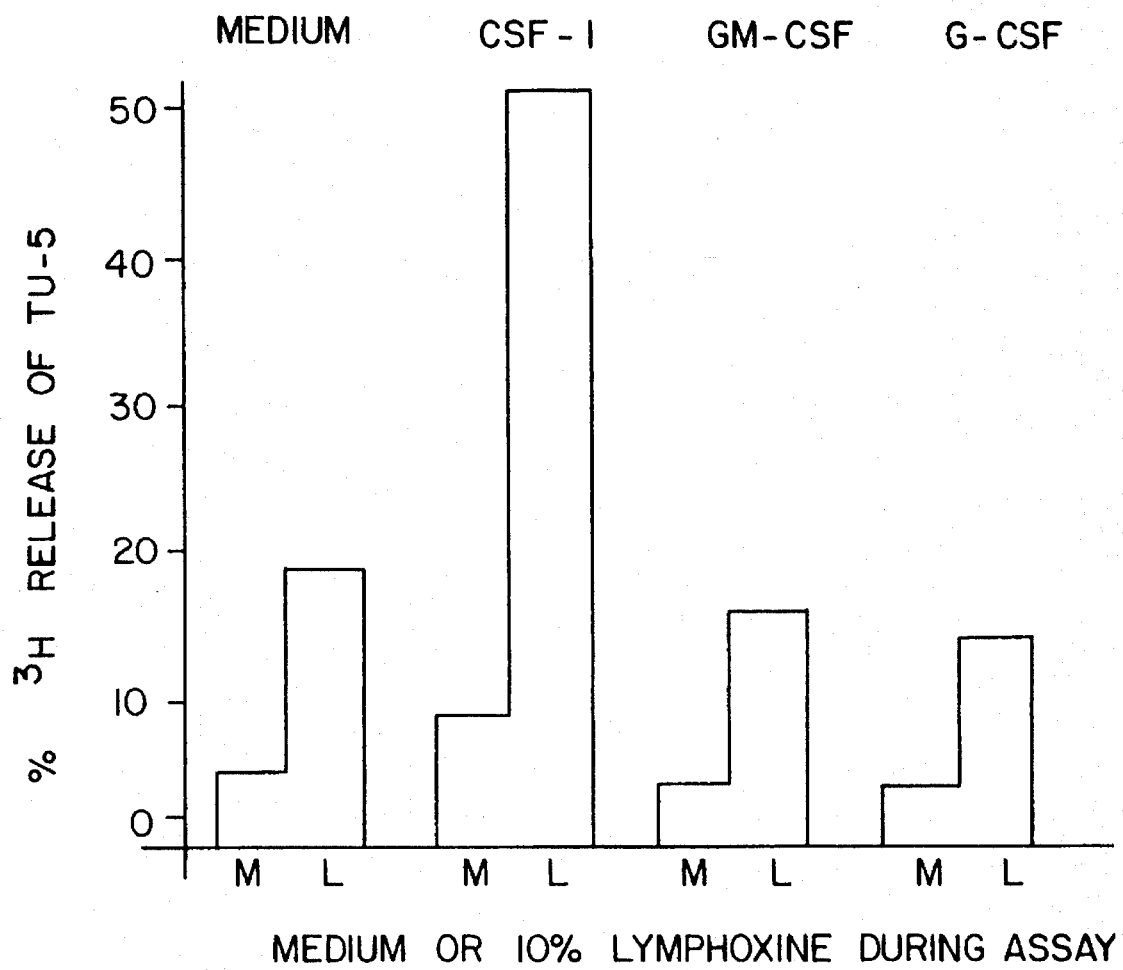
FIG. 1 shows a comparison of the activities of CSF-1 and other colony stimulating factors in enhancing the ability of macrophage to kill tumor cells.

"Colony stimulating factor-1 (CSF-1 or M-CSF)" refers to those proteins which exhibit the spectrum of activity understood in the art for CSF-1—i.e., when applied to the standard in vitro colony stimulating assay of Metcalf, D., *J Cell Physiol* (1970) 76:89, it is capable of stimulating the formation of primarily macrophage colonies. Native CSF-1 is a glycosylated dimer: dimerization is reported to be necessary for activity as the monomer is not active in the Metcalf colony stimulating assay (supra) or various other in vitro bioactivity assays (Ralph, P. et al, *Blood* (1986) 68:633; Stanley, E. R., et al, *J Biol Chem* (1977) 252:4305). As used herein the number of CSF-1 units corresponds to the number of colonies in the mouse bone marrow colony assay in the titratable range (described in Ralph et al, *Blood,* supra). Contemplated within the scope of the invention and within the definition of CSF-1 are both the dimeric and monomeric forms. The monomeric form may be converted to the dimeric form by in vitro provision of suitable refolding conditions as described in copending PCT WO 88/08003, published 20 Oct. 1988, and the monomer is per se useful as an antigen to produce anti-CSF-1 antibodies.

There appears to be some species specificity: Human CSF-1 is operative both on human and on murine bone marrow cells; murine CSF-1 does not show activity with human cells. Therefore, "human" CSF-1 should be positive in the specific murine radioreceptor assay of Das, 1981, supra, although there is not necessarily a complete correlation. The biological activity of the protein will generally also be inhibited by neutralizing antiserum to human urinary CSF-1 (Das, 1981, supra). However, in certain special circumstances (such as, for example, where a particular antibody preparation may recognize a CSF-1 epitope not essential for biological function, and which epitope is not present in the particular CSF-1 mutein being tested) this criterion may not be met.

Certain other properties of CSF-1 have been recognized more recently, including the ability of this protein to stimulate the secretion of series E prostaglandins, interleukin-1, and interferon from mature macrophages (Moore, R., et al, *Science* (1984) 223:178). The mechanism for these latter activities is not presently understood, and for purposes of definition herein, the criterion for fulfillment of the definition resides in the ability to stimulate the formation of monocyte/macrophage colonies using bone marrow cells from the appropriate species as starting materials, and under most circumstances (see above), show inhibition of this activity by neutralizing antiserum against purified human urinary CSF-1, and, where appropriate for species type, exhibit a positive response in the radioreceptor assay. (It is known that the proliferative effect of CSF-1 is restricted to cells of mononuclear phagocytic lineage (Stanley, E. R., *The Lymphokines* (1981), Stewart, W. E., II, et al, ed, Humana Press, Clifton, N.J.), pp. 102–132) and that receptors for CSF-1 are found on cells of this lineage (Byrne, P. V., et al, *Cell Biol* (1981) 91:848), placental trophoblasts and some other cells).

"Effective amount" signifies an amount effective to perform the function specified, such as to kill tumors or reduce tumor burden or prevent or cure infectious diseases.

"Therapeutic treatment" indicates treating a subject after a disease is contracted, and includes prophylactic therapy.

"Mammals," indicates any mammalian species, and includes rabbits, mice, dogs, cats, primates and humans, preferably humans.

"Expression system" refers to DNA sequences containing a desired coding sequence and control sequences in operable linkage, so that hosts transformed with these sequences are capable of producing the encoded proteins. In order to effect transformation, the expression system may be included on a vector; however, the relevant DNA may then also be integrated into the host chromosome.

As used herein "cell", "cell line", and "cell culture" are used interchangeably and all such designations include progeny. Thus "transformants" or "transformed cells" includes the primary subject cell and cultures derived therefrom without regard for the number of transfers. It is also understood that all progeny may not be precisely identical in DNA content, due to deliberate or inadvertent mutations. Mutant progeny which have the same functionality as screened for in the originally transformed cell are included. Where distinct designations are intended, it will be cl-ear from the context.

All patents, patent applications, and publications mentioned herein, both supra and infra, are hereby specifically incorporated by reference.

B. Embodiments of CSF-1

CSF-1 apparently occurs in numerous forms all of which are included in the embodiments of the present invention. Human CSF-1 cDNA clones coding for CSF-1 prepropolypeptides of three different lengths (256 amino acids; 554 amino acids; and 438 amino acids) have been isolated from cells expressing the single CSF-1 gene (see commonly owned U.S. Pat. Nos. 4,847,201 issued 11 Jul. 1989 and 4,868,119 issued 19 Sep. 1989; Wong, G. G., et al, *Science* (1987) 235:1504, Kawasaki, et al., *Science* (1985) 230:291; Ladner et al, *Embo J* (1987) 6:2693; Cerretti, D. P. et al, *Molecular Immunol* (1988) 25:761. The CSF-1 proteins useful in the therapies disclosed herein may also be processed by proteolysis including, for example, in the long form, at the Lys residue at 238, the Arg residue at 249, and the Arg residue at 411. It is believed that CSF-1 may occur in nature in one or more C-terminally deleted forms. In addition, CSF-1 proteins lacking the first two or four amino acids have been isolated in active form from the supernatant of the human cell line AGR-ON (equivalent CEM-ON; ATCC No. CRL-8199; Takahashi, M., et al. *Biochem Biophys Res Comm* (1988) 152:1401 and U.S. Pat. No. 4,675,291 issued 23 Jun. 1987). CSF-1 protein comprising monomers ending at amino acid 145 are reported to have in vitro biological activity (European Patent (EP) Publication No. 261,592 published 30 Mar. 1988). Some biological activity is reported for a dimeric CSF-1 protein composed of monomers ending at amino acid 132.(EP 328,061 published 16 Aug. 1989). The monomeric CSF-1 polypeptide (whether clipped at the C-terminus or not) may also refold to form multimers, most frequently dimers.

Native human urinary CSF-1 has been isolated as a highly glycosylated dimer of 45–90 kd, depending on the source, method of measurement and identity of the reporter. The recombinantly produced unglycosylated CSF-1 reported by Wong, et al, (supra) appears to have a monomeric molecular weight of approximately 21 kd. on the other hand, the molecular weight calculated on the basis of the amino acid sequence deduced for the "short" 224 amino acid form of CSF (SCSF) by Kawasaki et al, (supra) (see also U.S. Pat. No. 4,847,201 (supra) and commonly owned PCT Publication No. WO86/04607 published 14 Aug. 1986) is on the order of 26 kd, while that of the "long" 522 amino acid form (LCSF) is calculated to be on the order of 55 kd (Wong, et al. (supra); Ladnet et al (supra); commonly owned EP 272,779, published 29 Jun. 1988; and U.S. Pat. No. 4,868,119 corresponding to PCT Publication No. WO87/06954, published 19 Nov. 1987). When deleted constructs of these genes are expressed in *E. coli* (where glycosylation does not occur), they, of course, give rise to proteins of considerably lower molecular weight.

Other forms of CSF-1 proteins useful in the present invention include the polymer conjugated CSF-1 described in commonly owned U.S. Pat. No. 4,847,325. The transmembrane region deletion mutants disclosed in EP 249,477 published 16 Dec. 1987 and the glycosylation site deletion mutants disclosed in EP 272,779, supra, are also considered to be useful in the presently disclosed therapies.

Methods for the production of these various forms of CSF-1 from various sources are reported in U.S. Pat. No. 4,879,227 issued 7 Nov. 1989; WO 86/04587 published 14 Aug. 1986; WO 89/10407 published 2 Nov. 1989; WO 88/08003; supra and EP 276,551 published 3 Aug. 1988.

It is, of course, well known that bacterially produced mature proteins which are immediately preceded by an ATG start codon may or may not include the N-terminal methionine, and it is shown in EP 272,779 (supra) that deletion of residues 1 and 2 (both glutamic acid) or residues 1–3 (Glu—Glu—Val) aids in this manner. Deletions are noted by a $\nabla$ followed by the number of amino acids deleted from the N-terminal sequence, or by the number of amino acids remaining when residues are deleted from the C-terminal sequence. Thus, the N-terminal deletions referred to above having the first 2 and the first 3 residues deleted are designated N$\nabla$2 and N$\nabla$3, respectively. C-terminal truncations of CSF-1 resulting in proteins of 150, 158, 190 and 221 amino acids in length for example are referred to as C$\nabla$150, C$\nabla$158, C$\nabla$190 and C$\nabla$221, respectively. A 221 amino acid CSF-1 molecule derived from LCSF having an N-terminal deletion of 3 amino acids is denoted by LCSF/N$\nabla$3 C$\nabla$221, for example. Amino acid substitutions are designated by reference to the position of the amino acid which is replaced. For example, substitution of the cysteine residue at position 157 in FIG. 4 of Ladher et al, (supra) by serine is referred to as CSF-1Ser$_{157}$.

In summary, in addition to the N-terminal and C-terminal deletions and aggregations, individual amino acid residues in the chain may be modified by oxidation, reduction, deletion or other derivatization, and these proteins may also be cleaved and/or polymerized to obtain dimeric products that retain activity. Such alterations which do not destroy activity do not remove the protein sequence from the definition, and are specifically included as substantial equivalents. CSF-1 derived from other species may fit the definition of a protein having activity of "human CSF-1" by virtue of its display of the requisite pattern of activity as set forth above with regard to human substrate.

As is the case for all proteins, the precise chemical structure depends on a number of factors. As ionizable amino and carboxyl groups are present in the molecule, a particular protein may be obtained as an acidic or basic salt, or in neutral form. All such preparations which retain their activity when placed in suitable environmental conditions are included in the definition. Further, the primary amino acid sequence may be augmented by derivatization using sugar moieties (glycosylation) or by other supplementary molecules such as lipids, phosphate, acetyl groups and the like, more commonly by conjugation with saccharides, polyethylene glycols (PEGs), and polyoxyethylene glycols (POGs) as shown in U.S. Pat. No. 4,847,325. Certain aspects of such augmentation are accomplished through post-translational processing systems of the producing host; other such modifications may be introduced in vitro. In any event, such modifications are included in the definition so long as the activity of the dimeric protein, as defined above, is not destroyed. It is expected, of course, that such modifications may quantitatively or qualitatively affect the activity, either by enhancing or diminishing the activity of the protein in the various assays.

Further, individual amino acid residues in the chain may be modified by oxidation, reduction, or other derivatization, and the protein may be cleaved to obtain fragments which retain activity. Such alterations which do not destroy activity do not remove the protein sequence from the definition.

Modifications to the primary structure itself by deletion, addition, or alteration of the amino acids incorporated into the sequence during translation can be made without destroying the activity of the protein. Such substitutions or other alterations result in proteins having an amino acid sequence which falls within the definition of proteins "having an amino acid sequence substantially equivalent to that of CSF-1." Indeed, human- and murine-derived CSF-1 proteins have nonidentical but similar primary amino acid sequences which display a high homology.

C. General Description

The CSF-1 proteins of the invention are capable both of stimulating monocyte-precursor/macrophage cell production from progenitor marrow cells, thus enhancing the effectiveness of the immune system, and of stimulating such functions of these differentiated cells as the secretion of lymphokines in the mature macrophages.

In one application, these proteins are useful as adjuncts to chemotherapy. It is well understood that chemotherapeutic treatment results in suppression of the immune system. Often, although successful in destroying the tumor cells against which they are directed, chemotherapeutic treatments result in the death of the subject due to this side effect of these toxic agents on the bone marrow cells. Administration of CSF-1 to such patients, because of the ability of CSF-1 to mediate and enhance the growth and differentiation of bone marrow-derived precursors into macrophages and monocytes and to stimulate the function of these mature cells, results in a restimulation of the immune system to prevent this side effect, and thus to prevent the propensity of the patient to succumb to secondary infection.

CSF-1 may also be used to cure leukopenia, a disease involving a deficiency in the total number of white blood cells. Neutropenia reflects a deficiency affecting principally the polymorphonuclear leukocytes (neutrophils, granulocytes) and may be due to various infections, certain drugs (e.g., cytotoxic drugs) or ionizing radiations. Thus, in vivo administration of CSF-1 can be used to induce stem cells to indirectly increase the production of polymorphonuclear leukocytes, thereby increasing the count of white blood cells.

Other patients who would be helped by such treatment include those being treated for leukemia through bone marrow transplants; they are often in an immunosuppressed state to prevent rejection. For these patients also, the immunosuppression could be reversed by administration of CSF-1.

In general, any subject suffering from immunosuppression-whether due to chemotherapy, bone marrow transplantation, or other, forms of immunosuppression such as disease (e.g., acquired immune deficiency syndrome) would benefit from the availability of CSF-1 for pharmacological use. In addition subjects could be supplied enhanced amounts of previously differentiated macrophages to supplement those of the indigenous system, which macrophages are produced by in vitro culture of bone marrow or from blood monocytes, or other suitable preparations followed by treatment with CSF-1. These preparations include those of the patient's own blood monocytes or bone marrow derived cells, which can be so cultured and returned for local or systemic therapy.

The ability of CSF-1 to stimulate production of lymphokines by macrophages and to enhance their ability to kill target cells also makes CSF-1 directly useful in treatment of neoplasms and infections. Moreover, treatment of wounds with CSF-1 will promote tissue repair.

CSF-1 stimulates the production of interferons by murine-derived macrophage (Fleit, H. B., et al, *J Cell Physiol* (1981) 108:347), and human, partially purified, CSF-1 from MIA-PaCa cells stimulates the poly(I):poly(C)-induced production of interferon and TNF from human monocytes as illustrated in PCT publication WO86/04607, supra. In addition, CSF-1 stimulates the production of myeloid CSF by human blood monocytes.

Moreover, for the various uses described herein, CSF-1 can be employed in conjunction with other efficacious agents, including antibodies; lymphokines; cytokines; or macrophage activating agents, such as, e.g., IFN-alpha, IFN-beta, IFN-gamma, IL-2, TNF; or muramyl dipeptide and analogs thereof to treat tumors.

Also illustrated below is a demonstration of the ability of CSF-1 (from murine L-cell-conditioned medium and *E. coli* produced human recombinant CSF-1) to stimulate normal C3H/HeN mouse peritoneal macrophages to kill murine sarcoma TU5 targets. This activity is most effective when the CSF-1 is used as pretreatment and during the effector phase. The ability of CSF-1 to do so is much greater than that exhibited by other colony stimulating factors.

CSF-1 may also be employed to augment the lymphokine-induced antibody-dependent cellular cytotoxicity (ADCC) or targeted ADCC by macrophages or natural killer cells against tumor cells. This activity is particularly effective when CSF-1 is used in combination with IL-2, IFN-alpha, IFN-beta or IFN-gamma.

The ability of CSF-1 to enhance targeted ADCC activity is believed to be dependent on the kind of the antibody, the dose of CSF-1, and the effector to target ratio. Targeted cellular cytotoxicity is thought to rely on cell surface receptors on cytotoxic cells, such as monocytes, macrophages, natural killers, etc. It is known that the expression of one of these cell surface receptors, CD16, is enhanced by culturing these effector cells in CSF-1, with or without additional lymphokines, such as IL-2. If the cytotoxic cell is positioned up against the target cell, cytotoxicity is enhanced. A bifunctional antibody can promote this process by binding to a target cell through one of its combining sites, and to the lysis promoting receptor on the cytotoxic cell through its second combining site, thereby joining the two cell types and causing the cytotoxic cell to deliver a kill signal. "Bifunctional antibodies" include those produced by in vivo recombination of antibody chains in trioma or hybrid hybridoma cell lines and those produced by in vitro chemical conjugation of two antibodies or antibody fragments; the latter chemically linked antibodies are referred to as heteroconjugates.

In the instant invention, such bifunctional antibodies include either hybrid hybridoma derived bispecific or heteroconjugated antibodies that target the CD16 antigen known as the human Fc receptor III (FcRIII) on leukocytes. 3G8, a murine hybridoma secreting an $IgG_1$ monoclonal antibody to human FcRIII, is described in Unkeless, J. B., et al, *Ann Rev Imm* (1988) 6:251. The use of this antibody and monoclonal antibody 520C9 to develop a hybrid hybridoma derived bispecific antibody 2B1, is described in co-pending U.S. Ser. No. 07/249,710, filed 27 Sep. 1988. The resulting bispecific antibody exhibits binding to the CD16 Fc receptor III positive cells, as well as to breast cancer cells that display the positive proto-oncogene product erbB-2. 3G8 has also been chemically cross-linked (using chemical crosslinkers as described by, for example, Karpovsky, et al., *J. Exp Med* (1984) 160:1686) with 113F1 antibody, a murine monoclonal antibody to a breast cancer associated antigen (U.S. Pat. No. 4,753,894), producing an antibody also having bifunctional specificity.

The in vitro effective dose of CSF-1 in such a targeted cytotoxic assay, is in the range of 10–200 ng/ml. However its in vivo dosage is dependent upon various factors including the severity of the cancer, host immune status, body weight, the ratio of effector to target cells, many of which may only be determined on a case-by-case basis. CSF-1 should be administered in a dosage which does not cause a systemic toxic reaction but elicits the potentiating response on the effector cells.

The in vitro effective dosages of the bifunctional antibody are in the range of 1 ng/ml to 200 ng/ml. In vivo dosage again depends on a number of factors, including the clinical estimate of tumor size, the extent of metastasis and the biodistribution of the active drugs and of the cells that are activated. The effective in vitro effector to target cell ratio is approximately 10:1 to 80:1. The actual effector to target ratio in vivo depends on the accessibility of the tumors to the effector cells and antibodies.

In addition, the ability of murine cells to attack infectious organisms, including viruses such as those from the Herpesvirus genera, for example, cytomegalovirus; bacterial agents including those causing Gram-negative sepsis, and fungal infections, such as those caused by *Candida* and *Aspergillus* species, is enhanced by CSF-1. (Murine CSF-1 is inconsistently reported to stimulate murine macrophage to be cytostatic to P815 tumor cells (Wing, E. J., et al, *J Clin Invest* (1982) 69:270) or not to kill other leukemia targets (Ralph, P, et al, *Cell Immunol* (1983) 76:10). Nozawa, R. T., et al, *Cell Immunol* (1980) 53:116, report that a CSF-1 preparation may stimulate macrophage in vitro to ingest and kill *Candida*.)

Thus, in addition to overcoming immunosuppression per se, CSF-1 can be used to destroy the invading organisms or malignant cells indirectly or directly by stimulation of macrophage secretions and activity. This latter activity may be enhanced by adjunctlye CSF-1 therapy with an antimicrobial agent such as for example, antiviral, antifungal or antibacterial agents.

Finally, the CSF-1 may be used to promote the repair of tissues for wound healing when applied either locally or systemically. CSF-1 may recruit macrophages Wang, J. M., et al, *J Immunol* (1988) 141:575, as well as to induce them to provide connective tissue growth factors such as platelet-derived growth factor (PDGF), and active factors including tumor necrosis factor (TNF), as the stimulus for cell proliferation. Wound macrophages are reported to release substances that stimulate fibroplasia, collagen synthesis, and anglogenesis in vivo (Hunt T. K., et al, *Surgery* (1984) 96:48).

The CSF-1 of the invention may be formulated in conventional ways standard in the art for the administration of protein substances. Administration by injection is one preferred route; and such formulations include solutions or suspensions, emulsions, or solid composition for reconstitution into injectables or gel formulations. Suitable excipients include, for example, Ringer's solution, Hank's solution, water, saline, glycerol, dextrose, mannitol, solutions, and the like. While liquid solutions of CSF-1 may be used directly on or under wound dressings, reconstituted compositions are useful for salves, gel formulations, foams and the like for wound healing. Reconstituted gel formulations provide a controlled delivery system for CSF-1 at a wound site. Controlled release refers to drug release sufficient to maintain a therapeutic level over an extended period of time, such as up to 24 hours or more, preferably in the range of 24–72 hours. Increased contact time of growth factors may be necessary to achieve a significant increase in the rate of wound healing.

In addition, the CSF-1 of the invention may be preincubated with preparations of cells in order to stimulate appropriate responses, and either the entire preparation or the supernatant therefrom introduced into the subject. As shown hereinbelow, the materials produced in response to CSF-1 stimulation by various types of blood cells are effective against desired targets, and the properties of these blood cells themselves to attack invading organisms or neoplasms may be enhanced. The subject's own cells may be withdrawn and used in this way, or, for example, monocytes or lymphocytes from another compatible individual employed in the incubation.

As discussed previously and particularly with regard to the subject matter disclosed in U.S. Pat. No. 4,847,201 (supra), the complete coding sequences for a number of human CSF-1 proteins are now available, and expression vectors applicable to a variety of host systems have been constructed and the coding sequence expressed. In addition to those expression systems provided in U.S. Pat. No. 4,843,201, expression systems employing insect cells utilizing the control systems provided by baculovirus vectors have been described (Miller, D. W., et al, in *Genetic Engineering* (1986) Setlow, J. K. et al. eds., Plenum Publishing, Vol. 8, pp. 277–279, U.S. Pat. No. 4,745,051, issued 17 May 1988, and copending U.S. Ser. No. 077,188, filed 24 Jul. 1987. Insect cell-based expression can be in *Spodoptera frugiperda*. These systems are also successful in producing CSF-1. Mammalian expression has been accomplished in COS-7, CHO, mouse, and CV-1 cells, and also can be accomplished in COS-A2, hamster, and murine cells.

The variety of hosts available, along with expression vectors suitable for such hosts, permits a choice among post-translational processing systems, and of environmental factors providing conformational regulation of the protein thus produced. Thus, the availability of this information provides CSF-1 proteins in sufficient quantity for application in the various therapies discussed herein.

Among the vectors disclosed in the aforementioned patent publications, the plasmids pLCSF221A (which contains the gene encoding $asp_{59}$LCSF/NV∇3C∇221) and pcCSF-17 (which contains the gene encoding SCSF) are preferred for procaryotic and eukaryotic expression, respectively, of human CSF-1. The plasmid pCSF221A (hereinafter *E. coli* (221)) transformed into *E. coli* strain DG116, was deposited with the ATCC on 14 Apr. 1987 under accession no. 67390. The plasmid pcCSF-17 in *E. coli* MM294 was deposited with the ATCC on 14 Jun. 1985 under the accession no. 53149.

Also preferred are CSF-1 proteins which comprise the amino acid sequences containing the first 3–150 or 4–150 amino acids of SCSF and LCSF and the C-terminal deletions, such as LCSF/∇221.

D. Activity of CSF-1

The activity of CSF-1 was determined in the following examples using partially purified MIAPaCa CSF-1, murine L cell CSF-1, CV-1-produced recombinant material or *E. coli*-produced human CSF-1. CSF-1 was shown to enhance the production of interferon (IFN) and tumor necrosis factor (TNF) by induced human monocytes by up to 10 to 30-fold. CSF-1 also was demonstrated to stimulate macrophage antitumor toxicity in vitro, to inhibit tumor growth in vivo, to protect mice from lethal bacterial infection, to promote the repair of tissue damage in vivo, to inhibit the growth of cytomegalovirus in vivo, and to inhibit the growth of yeast in vivo.

The following examples are illustrative, not limiting, of the therapeutic uses claimed herein.

EXAMPLES

Stimulation of TNF Production by Human Monocytes

MIAPaCa CSF-1 was purified from the supernatant by calcium phosphate gel filtration and lentil lectin chromatography. For assay of lymphokine production, peripheral blood-adherent cells were incubated in duplicate flasks containing 10⁷ cells each. One flask was treated with 1000 U/ml CSF-1 purified as above. After 3 days, the cells were harvested, and washed, and resuspended at a cell concentration of $5 \times 10^5$/ml and plated in 24-well plates at 0.5 ml/well. The wells were treated with 10 ug/ml lipopolysaccharide (LPS) and 20 ng/ml PMA for 48 hr and the supernatants were harvested for TNF assay. Cells treated with CSF showed TNF secretions approximately ninefold higher than the untreated cells (1500 U/ml, compared to 162 U/ml).

Stimulation of Interferon Production by Human Monocytes

In an analogous experiment to determine the effect of CSF-1 on interferon production, peripheral blood-adherent cells were incubated for 3 days in the presence and absence of 1000 U/ml CSF-1, as described above, harvested, resuspended at $5 \times 10^5$/ml, and plated in a 24-well plate, as described above. The cells were induced for interferon production by addition of varying amounts of poly(I-):poly(C). The supernatants were assayed for interferon production by their cytopathic effect on VSV-infected GM 2504 cells. The CSF-1-stimulated cells showed production of 100 U/ml when induced with 50 ug/ml poly(I):poly(C), whereas comparably induced untreated cells produced less than 3 U/ml.

Stimulation of Myeloid CSF Production by Human Monocytes

Monocytes were incubated ± CSF-1 for 3 days and then induced for production of myeloid CSF as in Table 2. The three representative experiments shown used blood from different donors.

mixed at a 20:1 ratio with 3H-thymidine-labeled mouse sarcoma TU5 cells along with 10% v/v ConA-induced (10 ug/ml) spleen lymphokine (LK), which contains gamma interferon. The LK preparation can be replaced by purified gamma interferon in this assay. The release of labeled thymidine over the following 48 hr was used as a measure of tumor cell killing. The effect of adding CSF-1 as murine L-cell-conditioned medium containing 1200 U/ml CSF-1 is shown in the following table.

Purified murine CSF-1 and rhCSF-1 from CV-1 and *E. coli* (221) have also been effective in this assay.

| Treatment | | Kill | Increase Due |
|---|---|---|---|
| DAY 1 | DAY 13 | % | to CSF-1 % |
| — | — | 13 | |
| — | LK | 39 | |
| — | CSF-1 + LK | 49 | 26 |
| CSF-1 | LK | 51 | 31 |
| CSF-1 | CSF-1 + LK | 60 | 54 |
| — | — | 3 | |
| — | LK | 35 | |
| — | CSF-1 + LK | 47 | 34 |
| CSF-1 | — | 7 | |
| CSF-1 | LK | 49 | 40 |
| CSF-1 | CSF-1 + LK | 69 | 97 |

Increase in the ability to kill the target cells was noted whether CSF-1 was added during the preliminary 1 day of growth or during the period of induction; however, the most dramatic effects were observed when CSF-1 was present during both of these periods.

The possibility of contaminating bacterial LPS as the cause of stimulation of monocytes and macrophages was excluded: The LPS content of the applied CSF-1 was low (<0.3 ng/3000 U CSF-1, by Limulus amoebocyte lysate

TABLE 2

| | Myeloid CSF (U/ml) | | | | | |
|---|---|---|---|---|---|---|
| | Exp. 1 | | Exp. 2 | | Exp. 3 | |
| Induction | −CSF | +CSF | −CSF | +CSF | −CSF | +CSF |
| medium | 0 | 0 | 0 | 0 | 0 | 0 |
| 0.1 ug/ml LPS | — | — | 0 | 0 | 0 | 80 + 17 |
| 1 ug/ml LPS | 0 | 700 ± 72 | 40 ± 20 | 200 ± 20 | 103 ± 12 | 377 ± 57 |
| 0.1 ug/ml LPS + 2 ng/ml PMA | — | — | 617 ± 50 | 993 ± 101 | 1120 ± 82 | 1280 ± 60 |
| 1 ug/ml LPS + 2 ng/ml PMA | 283 ± 42 | 983 ± 252 | 360 ± 92 | 1400 ± 180 | 537 ± 47 | 1080 ± 122 |
| 2 ng/ml PMA | — | 370 ± 17 | 297 ± 6 | 183 ± 15 | 380 ± 52 | 716 ± 76 |

Therefore, CSF-1 stimulates myeloid CSF or colony stimulating activity production.

Stimulation of Tumor Cell Killing by Murine Macrophage; Comparison to other Colony Stimulating-Factors To assay macrophage stimulation, murine CSF-1 obtained from L-cell-conditioned medium, was used as a model for the recombinantly produced CSF-1 from pcCSF-17 in an assay which showed stimulation of the ability of murine macrophages to kill sarcoma targets. In this assay, 2 hr adherent C3H/HeN mouse peritoneal macrophages were incubated for 1 day in vitro with and without CSF-1 and then (LAL) assay); activity was removed by application to an anti-CSF-1 column; polymyxin B was used to neutralize LPS; the macrophages from C3H/HeJ mice respond to CSF-1 but not to LPS.

Effect of Other Myeloid CSFS

CSF-GM was prepared from 6 mouse lungs obtained 5 hours after IV administration of 5 ug LPS. The lungs were chopped and incubated for 3 days in serum free medium, and the supernatant was depleted of CSF-1 using a YYG106 affinity column (CSF-1 content reduced from 270 U/ml to 78 U/ml). CSF-G was prepared from similarly treated LD1 (melanoma cell line) serum free medium. Both CSF-GM and CSF-G contents were assayed at 2000 U/ml by colony stimulating assay.

The peritoneal macrophages were incubated with 40% of either of the foregoing media or with L-cell medium assayed at 2000 U/ml CSF-1 for 1 day, and then incubated for 48 hours either with additional medium or with LK, and assayed for TU5 killing as described above.

The results are shown in FIG. 1. While CSF-1 showed marked enhancement of toxicity to TU5, neither CSF-G nor CSF-GM had any effect.

In Vitro Test of CSF-1 as Stimulator of ADCC

CSF-1 purified from MIAPaCa cell line (approximately 40% purity, specific activity approximately $2 \times 10^7$ U/mg), murine L-cell conditioned medium (specific activity approximately $2.3 \times 10^5$ U/mg), and recombinant human (rh) from CV-1 (>95% purity, specific activity approximately $4 \times 10^7$ U/mg) were found to stimulate mouse macrophage ADCC to tumor targets in combination with IL-2 or. alpha-, beta- or gamma-IFN.

In the ADCC assay, female C3H/HeN or C3H/HeJ mice were injected i.p. with 1.5 ml proteose peptone (Difco Laboratories, Detroit, Mich.). After 3 days, the peritoneal exudate cells at $3 \times 10^5$ big cells/0.5 ml alpha-MEM medium plus 10% heat-inactivated fetal calf serum were adhered in replicate 1 ml wells in parallel sets. After 2 hr, the wells were washed thoroughly 3 times with PBS, and CSF-1 or lymphokine was added and incubated for 2 days at 37° C. The cell population was >95% macrophage by morphology and cell numbers recovered in parallel wells at day 2 were similar for the different treatments. On day 2, heat-inactivated antiserum (anti-Thy-1, rabbit anti-mouse brain, Accurate Chemicals, Westbury, N.Y.) was added to one of the parallel sets at various dilutions. The target, R1.1, a T-lymphoma cell line, was added to macrophage wells and to parallel wells without macrophages ± CSF-1, lymphokine, or antiserum.

Since high concentrations (1 ug/ml) of bacterial LPS stimulates macrophage ADCC, the murine and human CSF-1 preparations were tested using the LAL assay and had less than 0.2 ng/ml LPS.

The maerophages were then tested at 3:1 effector:target ratio for ADCC by introducing 105 R1.1 targets plus or minus antiserum and counting live target cells at 9, 24, 48 and 96 hr. Growth of R1.1 with control macrophages plus antibody was the same as that with control or cytokine-treated macrophages in the absence of antibody or that of R1.1 alone ± antibody ± cytokines.

| Macrophage Treatment | % ADCC* Kill with Time: | | |
|---|---|---|---|
| | 9 h | 24 h | 48 h |
| Medium | 0 | 0 | 0 |
| M-CSF | 0 | 0 | 0 |
| IFN-gamma | 44 ± 5 | 63 ± 3 | 72 ± 3 |
| M-CSF (1000 U) + IFN-gamma | 88 ± 1 | >96 | 98 ± 1 |
| M-CSF (100 U) + IFN-gamma | 83 ± 6 | 93 ± 3 | 92 ± 5 |

*%ADCC kill=100 (y−x)/y where y=target cell number minus antiserum and x=target cell number plus 1:20,000 dilution antiserum. IFN-gamma was used at 5 U/ml.

IFN-alpha and IFN-beta at 50 U/ml had about the same ADCC-stimulation effect as 5 U/ml IFN-gamma. IFN-alpha and IFN-beta at 5 U/ml had essentially no effect on ADCC, but in the presence of CSF-1 stimulated tumor killing to levels seen using 50 U/ml of either IFN alone. Similar effects were seen with rhIL-2: treatment of macrophages for two days with 5 U/ml IL-2 alone significantly boosted macrophage ADCC. CSF-1 moderately enhanced this strong IL-1 induced activity. However, when IL-2 was used at lower, ineffective concentrations of 1 U/ml or 0.2 U/ml, the addition of CSF-1 showed a strong enhancing effect on tumoricidal activity.

Other lymphokines were tested as primary stimulators of ADCC. Incubation of macrophages for two days with rhTNF at 1, 10 or 100 U/ml alone or with 1000 U/ml CSF-1 did not significantly induce ADCC activity. rhIL-1 alpha or beta at 0.2 to 50 U/ml and murine rIL-4 at 1 to 100 U/ml also did not stimulate ADCC alone or with CSF-1. Attempts were made to find other cofactors which could substitute for CSF-1. Murine rGM-CSF and rIL-3 tested at 10, 100 or 1000 U/ml did not boost ADCC alone or with IFN-gamma in the standard two-day pretreatment of macrophages, in contrast to CSF-1. These cytokines, after incubation 2 days in medium, had no effect on growth of R1.1 targets in the absence of macrophages.

In Vitro Targeted ADCC Assays

The effects of CSF-1 on cultured human peripheral blood monocytes were studied to determine whether pretreatment with CSF-1 could enhance targeted ADCC.

Human effector cells were isolated from donor buffy coats obtained from Stanford University Blood Bank (Palo Alto, Calif.). Mononuclear cells were separated by Ficoll-Hypaque differential centrifugation..To isolate adherent mononuclear cells (AMC), total mononuclear cells were plated into 24-well tissue culture plates and allowed to adhere for 30 min at 37° C., 5% $CO_2$. Nonadherent cells were washed off with warm Hank's balanced salt solution with 50 ug/ml gentamicin. The viabilities of all effector cell preparations were >95% by trypan blue dye exclusion. Adherent mononuclear cells were stained with FITC-anti LeuM3 (Becton Dickinson, Mountain View, Calif.) and analyzed on an EPICS V cell sorter to be >85% LeuM3 positive.

The antibody heteroconjugate 113F1 F(ab')$_2$-3G8 F(ab')$_2$, a chemically linked antibody recognizing both a breast cancer associated antigen and the human FcRIII (CD16), and the hybrid hybridoma derived bispecific antibody 2B1, which has anti-CD16 and anti-erbB-2 activities, were used in the following experiments. Both of these antibodies mediate good specific lysis of SK-Br-3 tumor target cells using human total mononuclear cells as effectors.

One day before an ADCC assay, target cells in T75 flasks (50% confluent) were labeled with 62.5 uCi of $^3$H thymidine (New England Nuclear, 6.7 uCi/mmole) in 25 ml medium. After 30 hours, the cells were trypsinized off the flasks and washed 3 times. Forty thousand labeled target cells were used per well in the assays.

Medium used throughout the assays for diluting effector cells, antibodies and CSF-1 was AIM.V serum free medium (Gibco) with 8 mM glutamine. Final total volume was 1 ml/well. For CSF-1 treatment, medium with or without CSF-1 was added to effector cells and incubated for 2–3 days. Antibodies and labeled target cells were then added. Tritium release in the supernatant was measured after 3 days with Cytoscint (ICN) as the scintillation fluid.

Each sample was tested in 4 replicates in each experiment. The well to well variation of the replicates was usually less than ±20% of the mean value. The mean tritium release of the replicates was used to calculate the percent specific lysis, using the formula: (mean sample release-spontaneous release)/(maximum release-spontaneous release). To measure spontaneous release, labeled target cells were incubated in medium alone, and the supernatant was counted after 3 days. Spontaneous release of tritium from the target cells (in the absence of effector cells) averaged less than 10% in all experiments. Neither antibodies nor CSF-1 increased spontaneous lysis when incubated with the target cells alone. To measure maximum release, labeled target cells were lysed in a final concentration of 0.5% SDS.

Figure 2:
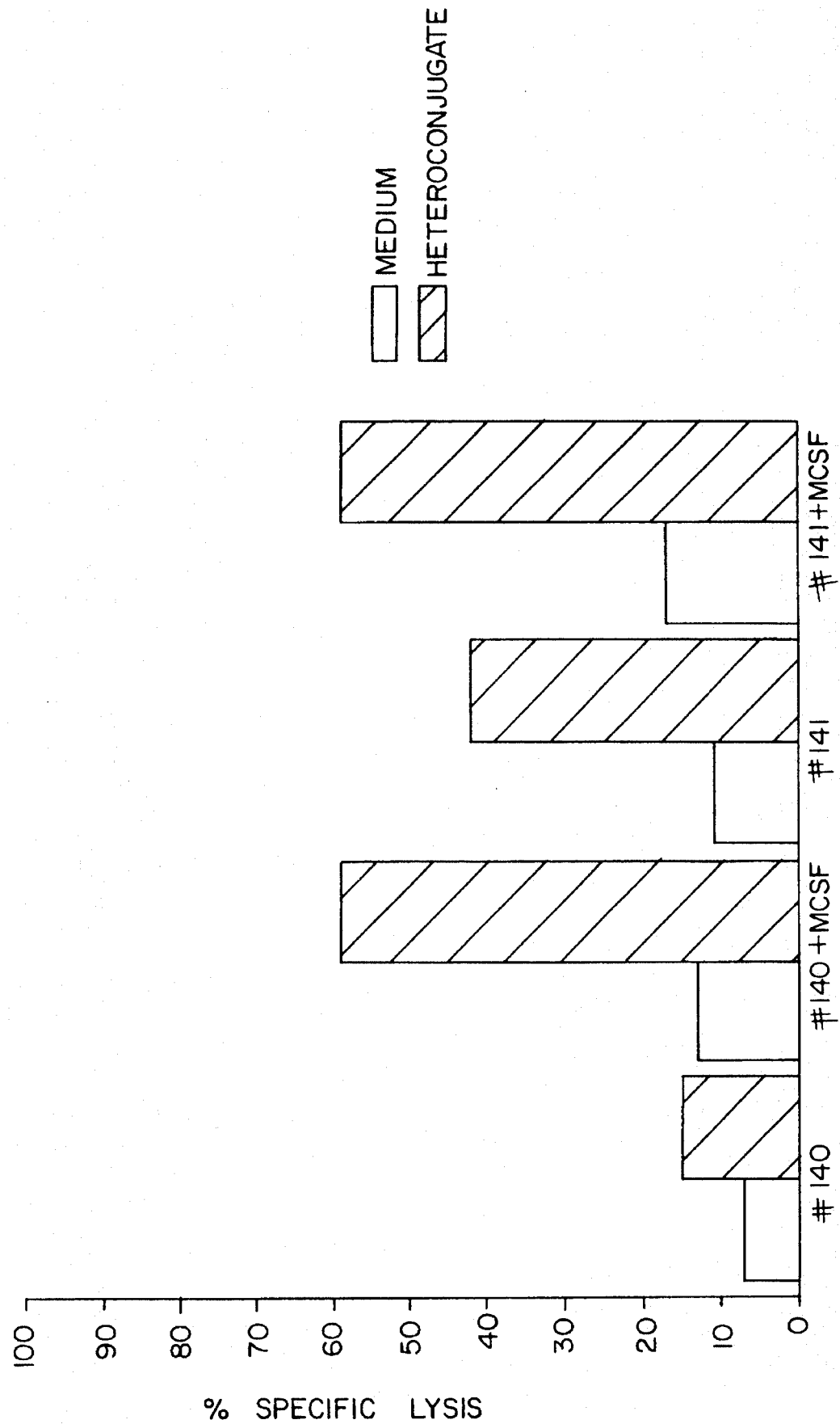
FIG. 2 shows the ability of the heteroconjugate antibody 113F1 F(ab')$_2$-3G8 F(ab')$_2$ at 1 ug/ml to mediate lysis of cancer cells by adherent blood mononuclear cells (AMC) in the presence and in the absence of CSF-1.
Figure 3:
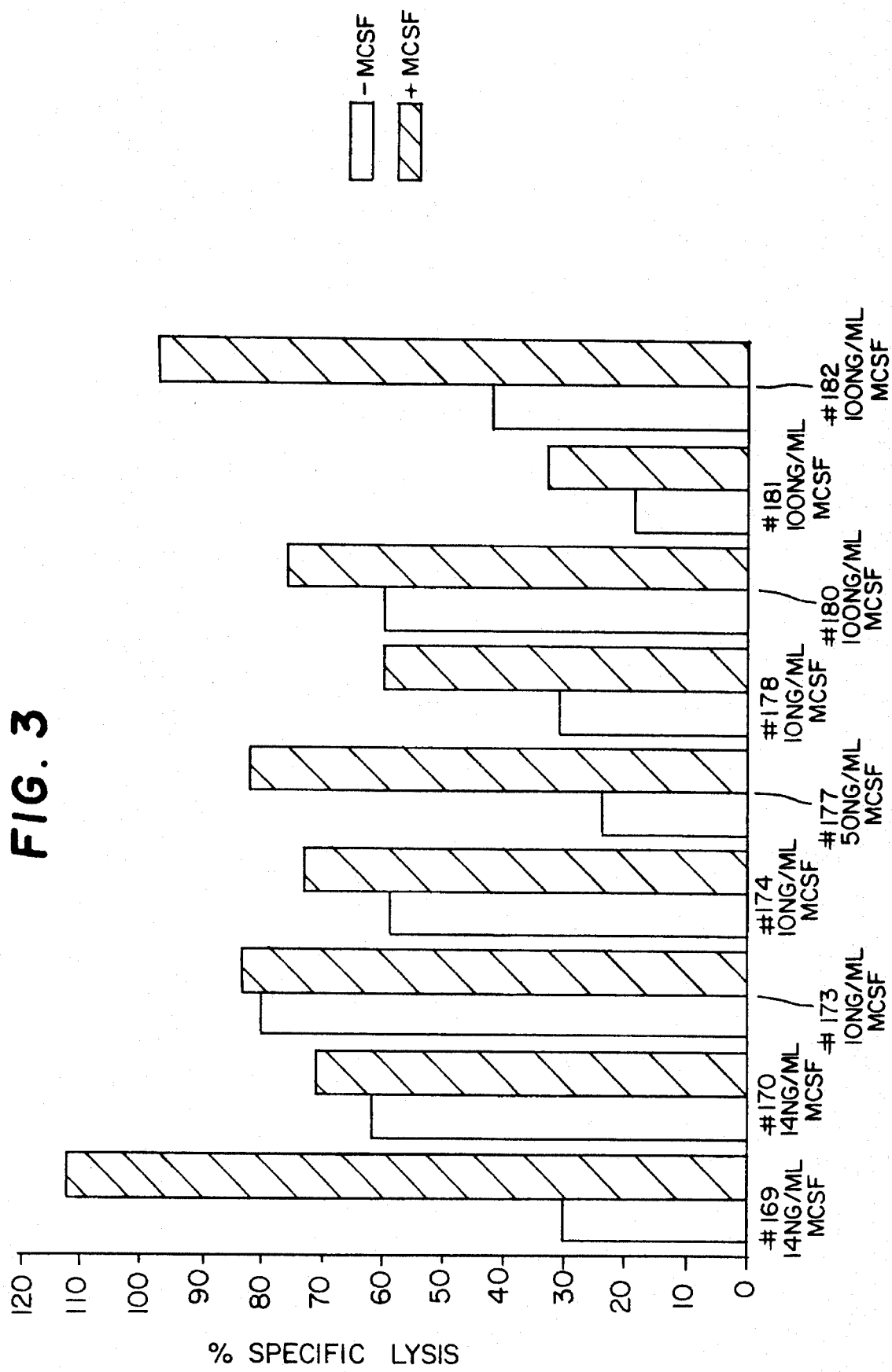
FIG. 3 shows the ability of the bispecific antibody 2B1 to mediate lysis by AMC preincubated with 14–100 ng/ml of CSF-1, as compared to antibody alone.

The ability of the heteroconjugate 113F1 F(ab')$_2$-3G8 F(ab')$_2$ at 1 ug/ml to mediate lysis with AMC from two donors is shown in FIG. 2. When AMC plus the heteroconjugate were tested against SK-Br-3 at an E:T ratio of 20:1, the average antibody dependent lysis observed was 28%. As shown in this figure, when the effector cells were preincubated with 14 ng/ml of CSF-1 heteroconjugate mediated lysis was enhanced by approximately 110%.

Figure 4:
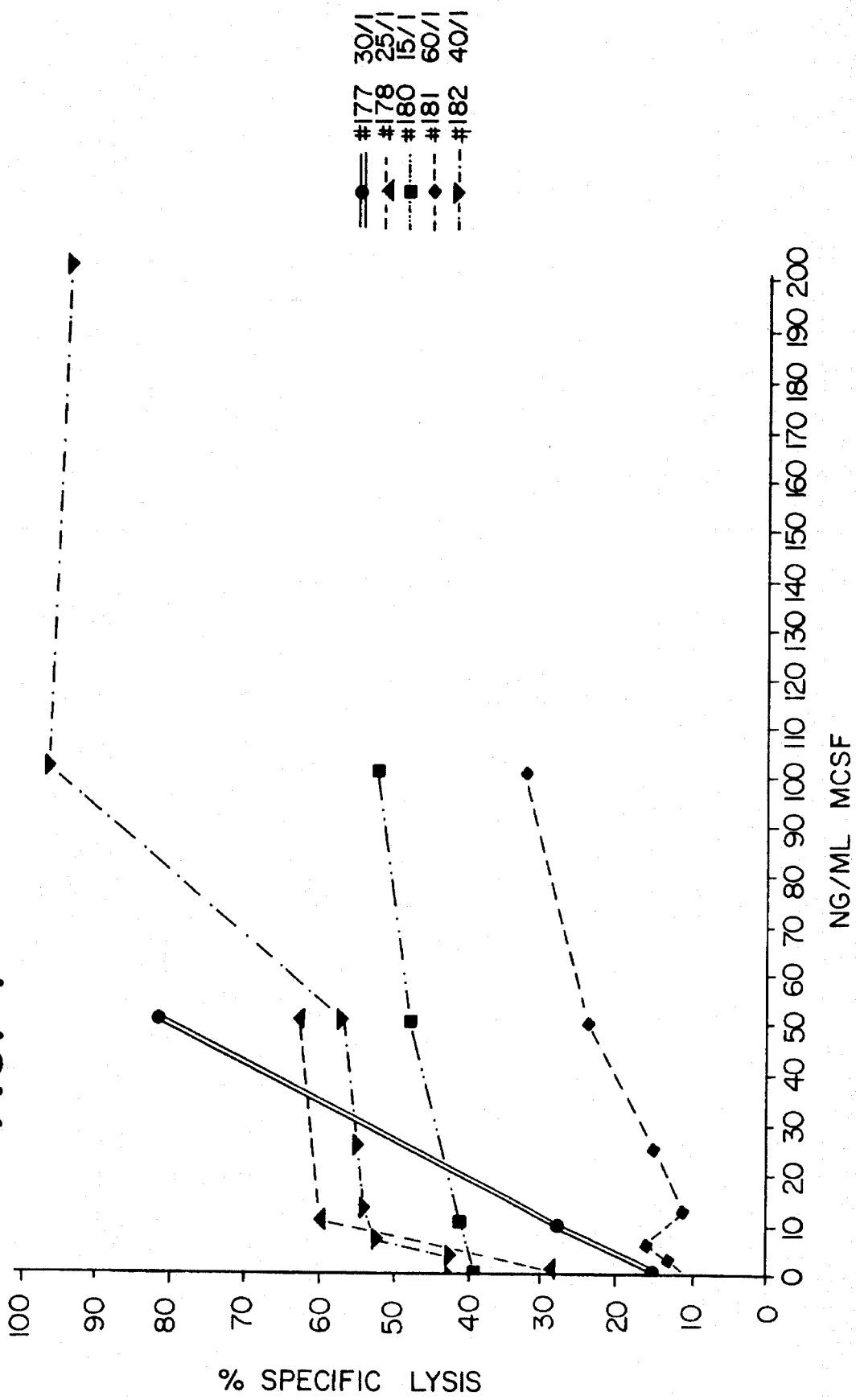
FIG. 4 shows the results of CSF-1 dose range studies on AMC using 100 ng/ml of 2B1.

Adherent cells from a total of 11 donors were tested with the F(ab')$_2$ fragment of bispecific antibody 2B1. To avoid the possible involvements of FcRI and FcRII on human AMC, 2B1 F(ab')$_2$ was used in the study instead of whole 2B1. (An experiment was also conducted to show that the F(ab')2 fragments of the 2 parental antibodies of 2B1; 520C9 and 3G8, did not mediate any specific lysis whereas 2B1 F(ab')$_2$ caused almost complete lysis of the target cells.) The effects of CSF-1 at 10–100 ng/ml were studied to observe whether CSF-1 was effective in augmenting lysis mediated by 2B1 F(ab')$_2$. AMC preincubated with 14 to 100 ng/ml of CSF-1 gave higher specific lysis than AMC preincubation without CSF-1 (IFIG. 3). The total amount of target cell lysis obtained varied from donor to donor, although increases in specific lytic activity with CSF-1 treatment were reproducibly observed in all monocyte preparations. As higher levels of csF-1 may be necessary to stimulate the AMC of minimally responsive or unresponsive donors, CSF-1 dose response studies were conducted using 100 ng/ml of 2B1 F(ab')$_2$ and the results are shown in FIG. 4. Preincubating AMC with increasing concentrations of CSF-1, prior to introduction of 2B1 F(ab')$_2$, gave higher specific lysis starting at 10 ng/ml and did not yet plateau at 100 ng/ml in all donors.

In Vivo Test of CSF-1 for Anti-Tumor Efficacy

A. Meth A Sarcoma Model

Recombinantly produced CSF-1 (158) from CV-1 cell line (LAL assay:2 ng LPS/ml, 8 ng LPS/mg CSF, 2×10$^7$ units/mg) was injected intraperitoneally at 50 ug/dose twice a day for five days into a 20 g mouse (3 mice per group) implanted subcutaneously with a Meth A sarcoma tumor 7 days earlier. For six days after the beginning of the CSF-1 treatment, the three untreated and three treated mice were evaluated for body weights and tumor volumes. There was no evidence of toxicity as measured by change in body weight. On day 7, one mouse from each group was sacrificed for comparative histopathological analysis (no gross signs). The four remaining mice were evaluated for the usual 14-day period in the Meth A model. The results are provided in the table below:

| | Mean Change in Tumor Volume (Δ TV) | | |
|---|---|---|---|
| | Treatment | | % Treated/ |
| Day | CSF-1 | Buffered Saline | Δ Control |
| 3 | 2.0 | 2.2 | 91 |
| 6 | 2.6 | 6.8 | 38 |
| 7 | 4.1 | 8.0 | 51 |
| 8 | 5.7 | 11.0 | 52 |
| 14 | 13.9 | 29.4 | 47 |

Δ TV = Ratio of the mean tumor volume at the day indicated to the mean tumor volume at day 0 within a single group of mice.

The results show that there was evidence for CSF-1-mediated efficacy, particularly at the day 6 tumor volume measurements. The differences between the CSF-1 and control groups were greatest during a period starting several days after the commencement of treatment and several days thereafter, after which the tumor returned to its usual rate of growth. These data suggest that multiple daily dosing (continuous infusions to improve efficacy at this dose level, for longer periods of time) or a higher dose level and altered schedule to include drug holiday may enhance efficacy.

Similar results were seen using LCSF CΔ190, and LCSF C 221 from E. coli. The protocol was performed using a group of 5 mice; 50 ug/dose of each product were used and the administration (twice daily for 5 days) was similar except for the E. coli 150 and 190 material wherein the schedule was increased to 10 days and administration was 7–8 hrs apart. The following table provides results as a percentage of ∇TV Treated divided by ΔTV Control for each CSF-1-derived material.

| Day | (C 158) CV-1 | C∇150 | C∇190 | C∇221 | N∇3 C∇221 |
|---|---|---|---|---|---|
| 3 | 21 | 0 | 0 | 36 | 14 |
| 4 | 23 | 0 | 0 | 38 | 46 |
| 5 | 46 | 5 | | 44 | 48 |
| 6 | 59 | 7 | 57 | 50 | 40 |
| 7 | 61 | 15 | 70 | 61 | 40 |
| 8 | 64 | 7 | 81 | 40 | 39 |
| 13/14 | 56 | 30 | 28 | 20 | 26 |

B. B16 Metastases Model

CSF-1 was tested in the B16 experimental metastasis model to assess its effect on the prevention of pulmonary metastases.

1×10$^5$ tumor cells, suspended in 0.2 ml of Ca$^{+2}$ and Mg+2-free HBSS, were inoculated into unanesthetized mice in the lateral tail vein. Twenty-one days after tumor cell inoculation, the mice were sacrificed and necropsied. During necropsy, the lungs and brain were removed, rinsed in water, and weighed. The lungs were then fixed in Bouin's solution, and the number of surface tumor nodules per pair of lungs was determined with the aid of a dissecting scope.

Recombinant human CSF-1 (N∇3C∇221, was used for all experiments. CSF-1 was freshly obtained prior to each experiment from frozen stocks and diluted immediately prior to injection in USP 0.9% saline. CSF-1 was delivered intravenously on a once a day (QD)×10 day schedule. The dosing levels used are given in the following table. As a negative control consisting of a non-specific and non-therapeutic protein, either USP human serum albumin (HSA) or boiled CSF-1 was used. CSF-1 was boiled for 30 min to inactivate the CSF-1 activity. The efficacy data demonstrates that CSF-1 given QD ×10, intravenously, starting 3 days before intravenous inoculation of 1×10⁵ tumor cells produces a significant reduction in the median number of pulmonary metastases. In contrast, if the CSF-1 therapy was initiated one day post tumor cell inoculation, no significant decrease in the median number of pulmonary metastases was observed. No overt toxicity, as measured by lethality, was observed at this dose level (2.5–5.0 mg/kg).

| Group | Dose | Day of Initiation of Therapy | Median Number of Pulmonary Metastases (Range) |
|---|---|---|---|
| 1. Saline | — | +1 | 55 (5, 29, 48, 52, 52 58, 58, 74, 80, 91) |
| 2. M-CSF | 2.5 mg/Kg | +1 | 38 (11, 11, 13, 28, 32, 44, 50, 64, 67, 90) |
| 3. M-CSF | 5 mg/Kg | +1 | 50 (22, 32, 48, 48, 48, 52, 57, 62, 65, 76) |
| 4. M-CSF | 2.5 mg/Kg | −3 | 7[a] (0, 0, 2, 5, 6, 8, 9 11, 12, 19) |

[a]Difference is significant between this group and control at p = 0.002 (Mann-Whitney).

In a second experiment, CSF-1 was administered i.v. QD×5. B16-W10 tumor cells were harvested by a brief one min trypsinization, centrifuged, and then prepared as a single cell suspension in Ca- and Mg-free HBSS. On day 0, 8 ×10⁴ cells were injected per mouse, in a total volume of 0.2 ml in the lateral tail vein. CSF-1 (*E. coli* N∇3C∇221) therapy (0.25 to 5.0 mg/kg/day) was administered QD×5, i.v., beginning on day −3. On day 14 the mice were sacrificed, the lungs removed, rinsed in water, and then fixed on Bouins fixative. Surface tumor nodules were counted with the aid of a dissecting scope. As shown below, CSF-1 was able to significantly decrease the median number of pulmonary metastases when administered i.v. at either 1.0, 2.5 or 5.0 mg/kg/day, QD×5.

| GROUP | DOSE (mg/kg/day) | # LUNG METASTASES Median (individual values) | p-VALUE |
|---|---|---|---|
| HSA | 5.0 | 199.5 (94, 142, 176, 181, 187, 212, 221, 223, 236, 250) | — |
| CSF-1 | 5.0 | 27.0 (2, 4, 11, 18, 25, 29, 31, 33, 39, 98) | 0.000 |
| CSF-1 | 2.5 | 132.0 (12, 33, 43, 67, 105, 159, 161, 178, 206, 239) | 0.034 |
| CSF-1 | 1.0 | 85.5 (19, 61, 62, 64, 64, 107, 114, 160, 201, 234) | 0.013 |
| CSF-1 | 0.5 | 173.5 (23, 114, 127, 159, 171, 176, 191, 194, 200, 236) | 0.173 |

80,000 tumor cells IV on day 0
Treatment: HSA or M-CSF QD × 5 IV beginning day 3
10 BDF-1 mice/group, sacrificed on day 14

The following experiment shows that CSF-1 may be administered by the subcutaneous (s.c.) or intraperitoneal (i.p.) route which are equally effective as CSF-1 when administered i.v.

Tumor cells were prepared as taught above. On day 7.5×10⁴ cells were injected per mouse (5–10 female BDF-1 mice/group), in a total volume of 0.2 ml in the lateral vein. CSF-1 at 5 mg/kg/day, QD×5 beginning on day −3 was administered by the three different routes. On day 18 the mice were sacrificed and the lungs were prepared as taught above. The results are shown below.

| Group[a] | Route | # Lung Metastases Median | Individual values |
|---|---|---|---|
| 1. HSA | i.v. | 26.5 | 0, 1, 19, 20, 26, 27, 35, 43, 59, 76 |
| 2. M-CSF | i.v. | 1.0 | 0, 0, 1, 10, 30 |
| 3. HSA | i.p. | 22.0 | 16, 17, 22, 33, 34 |
| 4. M-CSF | i.p. | 1.0 | 0, 1, 1, 3, 4[b] |
| 5. M-CSF | s.c. | 2.0 | 0, 1, 2, 2, 9[b] |
| 6. HSA | i.v. | 85.5 | 2, 8, 23, 30, 50, 61, 64, 68, 73, 84, 87, 91, 91, 93, 98, 112, 147, 150, 150, 150 |
| 7. M-CSF | i.v. | 6.0 | 0, 1, 2, 5, 5, 7, 7, 13, 15, 18[b] |
| 8. M-CSF | i.v. | 2.0 | 0, 0, 0, 1, 1, 3, 4, 4, 6, 33[b] |
| 9. M-CSF | s.c. | 2.5 | 0, 0, 0, 2, 2, 3, 3, 4, 4, 72[b] |

[a]Groups 6–9 were run in a separate experiment from Groups 1–5
[b]p-value is less than 0.05 compared to the proper HSA control The following experiment compares the efficacy of CSF-1 administered by continuous infusion performed subcutaneously using Alzet osmotic pumps and subcutaneous bolus dosing. CSF-1 was administered either as a s.c. bolus or as a s.c. continuous infusion in 0.9% NaI. Continuous infusions were performed using s.c. implanted Alzet pumps, models 1003D and 2001, which delivered CSF-1 for either 3 days or 14 days, respectively. The 1003D model pump has a mean pumping rate of 1 ul/hour and a mean fill volume of 87 ul. The 2001 model pump has a mean pumping rate of 0.417 ul/hour and a mean fill volume of 207 ul. For pump implantation, BDF-1 female (18–20g) were anesthetized with Metofane and a small dorsal incision was made in the skin. Pumps were implanted under the skin with the flow moderator pointing away from the incision. The incision was closed with a wound clip. All therapy was initiated on day −3.

On day 0, to 7.5×104 B16-W10 tumor cells (prepared as previously described) were injected per mouse, in a total volume of 0.2 ml in the lateral tail vein using a 27-gauge needle. On day 18, the mice were sacrificed, the lungs removed, rinsed in water, and then fixed in Bouins fixative.

As shown in the following table, CSF-1 administered by s.c. continuous infusion at doses as low as 0.25 mg/kg/day was highly effective at decreasing the median number of pulmonary metastases.

| GROUP | DAILY DOSE mg/kg | ROUTE[a] | SCHEDULE | Lung Metastases Median | (Individual values) | p-Value vs HSA | vs s.c. bolus |
|---|---|---|---|---|---|---|---|
| 1. HSA | 1.0 | s.c. | QD × 14 d-3 | 58.5 | (21, 27, 54, 58, 59, 66, 71, >100, 100) | — | — |
| 2. HSA | 1.0 | 14d pump | d-3 | 56.0 | (2, 40, 40, 42, 44, 68, 69, 87, >100, 100) | — | 0.820 |
| 3. CSF-1 | 1.0 | s.c. | QD × 14 d-3 | 37.0 | (4, 25, 26, 28, 33, 41, 42, 75, >100, 100) | 0.305 | — |
| 4. CSF-1 | 1.0 | 14d pump | d-3 | 9.5 | (2, 5, 6, 7, 9, 10, 21, 21, 24, 36) | 0.002 | 0.005 |

-continued

| GROUP | DAILY DOSE mg/kg | ROUTE* | SCHEDULE | Lung Metastases Median (Individual values) | | p-Value vs HSA | vs s.c. bolus |
|---|---|---|---|---|---|---|---|
| 5. CSF-1 | 0.5 | s.c. | QD × 14 d-3 | 66.5 | (28, 32, 36, 45, 65, 68, 81, >100, 100, 100) | 0.849 | — |
| 6. CSF-1 | 0.5 | 14d pump | d-3 | 19.0 | (2, 11, 15, 16, 19, 20, 25, 34, 35) | 0.002 | 0.000 |
| 7. CSF-1 | 0.25 | 14d pump | d-3 | 14.0 | (0, 5, 8, 10, 11, 17, 20, 25, 28, 48) | 0.005 | — |
| 8. CSF-1 | 5.0 | i.v. | QD × 5 d-3 | 12.0 | (0, 0, 2, 10, 11, 13, 14, 15, 52, 91) | 0.015 | — |

*Mice were implanted with Alzet osmotic pumps subcutaneously.

These studies suggest that CSF-1 when administered by s.c. continuous infusion is at least 10-fold more potent than the same dose given over the same period of time by once a day s.c. boluses.

In Vitro Test of CSF-1 Alone and with IFN-gamma for Anti-Tumor Efficacy

The protocol set forth below is substituted for the example in U.S. Ser. No. 99,872, filed 22 Sep. 1987, documenting the in vitro cytotoxic effect of CSFi1 alone and with IFN-gamma on A375 malignant human melanoma cell line target cells. The present example tested a number of cytokines, besides CSF-1 and IFN-gamma, for enhancement of tumor cell cytotoxicity.

Mononuclear cells (MNC) were separated from either heparinized venous blood or buffy coats of normal healthy volunteers by density gradient centrifugation on lymphocyte separation medium (LSM-Organon Teknika Corp., Durham, N.C.). MNC were then Washed twice with PBS and layered on 49.2% isotonic Percoll (Pharmacia) and centrifuged for 25 minutes at 1500×G. The monocyte band at the interface ($\geq$80% pure monocytes by morphological analysis of cytocentrifuge preparations) was harvested and further purified by plastic adherence at 37° C. Adherence was done in 96 well plates at a density of $1.2 \times 10^5$ cells per well. After one hour, non-adherent cells were removed by vigorous washing, leaving approximately $1 \times 10^5$ cells per well.

Purified monocytes were cultured for three days in 0.1% FCS containing either CSF-1 (*E. coli* N$\nabla$3C$\nabla$221), IL-1, IL-3, IL-4, GM-CSF (all from Genzyme Corp.), IL-2 (Cetus Corp.), or medium alone (1° induction). After three days, monocytes were washed and then incubated for an additional two days with 2° inducers. 1° induction with or without CSF-1 was also carried out in flasks in several experiments. Monocytes were adhered directly in tissue culture flasks, non-adherent cells were removed, and 1° inducers were added. After the 1° induction, monocytes were harvested by trypsinization and gentle scraping; viable cell counts were done by trypan blue exclusion, and $1 \times 10^5$ cells per well were plated in 96 well plates for the remaining two days of the protocol.

The WEHI 164 tumoricidal assay (Colotta et al, *J Immunol* (1984) 132:936) was used to test the cytotoxicity of the cytokines. Briefly, WEHI 164 target cells in active log phase were either pre-treated for three hours with actinomycin D (act D) at 1 ug/ml, washed, and labeled for one hour with 200 uCi of $^{51}$Cr, or treated simultaneously with act D and $^{51}$Cr for one hour at 37° C. in 5% $CO_2$. After removing 100 ul of culture supernatant from the monocytes, labeled target cells were added in a 100 ul volume to the effector cells to achieve an effector to target ratio of 10:1, unless otherwise noted. The cells, in a volume of 200 ul, were allowed to incubate for six hours at 37° in 5% $CO_2$. The plates were then centrifuged for five minutes at 1200 rpm in a table-top swinging bucket centrifuge. 100 ul of supernatant was removed from each well and counted in a gamma counter.

P815 target cells were treated similarly, except the actinomycin D pre-treatment was omitted, and the target cells and effector cells were co-incubated for 18 hours.

Percent induced cytotoxicity was calculated using the formula:

$$\frac{\text{experimental cpm} - \text{spontaneous cpm}}{\text{maximum cpm} - \text{spontaneous cpm}} \times 100$$

where:

experimental cpm=effector cells+target cells+inducers spontaneous cpm=effector cells+target cells+media maximum cpm=target cells alone lysed with 1% SDS The results are shown in the following tables:

| Percent Cytotoxicity Induced by CSF-1 | | | |
|---|---|---|---|
| | Induction Protocol | | |
| 1° | media | CSF-1 | CSF-1 |
| 2° | CSF-1 | CSF-1 | media |
| Experiment 1 | 19% | 34% | 35% |
| Experiment 2 | 12% | 49% | 37% |
| Experiment 3 | 4% | 8% | 5% |
| Experiment 4 | 7% | 19% | 9% |

Although the level of activation induced by CSF-1 was variable, 16 out of 40 such donors showed between 10% and 49% enhanced tumoricidal activity upon stimulation by CSF-1 alone.

In the following table, CSF-1 was used as a 1° inducer prior to addition of a variety of 2° inducers.

| | % Cytotoxicity | |
|---|---|---|
| 2° Stimulation | 1° Stimulation | M-CSF at 1000 U/ml |
| Medium Control | 0 | 2 |
| M-CSF 1000 U/ml | 1 | 11 |
| LPS 1 ug/ml | 4 | 26 |
| IFN-gamma 1 U/ml | 0 | 7 |
| IFN-gamma 100 U/ml | 2 | 13 |
| LPS 1 ug/ml + IFN-gamma (1 U/ml) | 11 | 29 |
| LPS 1 ug/ml + IFN-gamma (100 U/ml) | 7 | 49 |
| LPS 1 ug/ml + PMA 2 ng/ml | 22 | 53 |
| LPS 10 ug/ml + PMA 2 ng/ml | 24 | 45 |
| IL-2 50 U/ml | 2 | 5 |
| IL-2 500 U/ml | 2 | 7 |

Other factors tested as 2° inducers and found to have no effect with or without CSF-1 included IL-1, IL-3, IL-4 and GM-CSF at up to 500 U/ml.

In Vitro Stimulation of Murine Antiviral Activity

Adherent murine thioglycolate-elicited macrophages were incubated with CSF-1 for 3 days and infected with VSV overnight (Lee, M. T., et al, J Immunol (1987) 138:3019–3022). The following table shows crystal. violet staining as measured by aDsorbance at 550 nm of cells remaining adherent.

| Treatment | Absorbance (mean) (S.D.) |
|---|---|
| Medium/No virus | 0.34 ± 0.02 |
| Medium + virus | 0.170 ± 0.02 |
| CSF-1, 1000 U/ml + virus | 0.264 ± 0.02 |
| CSF-1, 2000 U/ml + virus | 0.365 ± 0.04 |

CSF-1 treated cells, therefore, showed protection of the macrophage against VSV.

In Vivo Treatment of CMV Infection with CSF-1

Outbred CD-1 mice were treated with the CSF-1 (158) produced from the CV-1 cell line at doses of 400 ug/kg, intraperitoneally, once a day for five days, starting two days before infection with a sub-lethal dose of cytomegalovirus (CMV). Mice were sacrificed on the third day after infection and the extent of viral replication in target organs such as the spleen was evaluated by plaque assay. The results showed that mice treated with CSF-1 have significantly lowered (57.8% reduction in) spleen vital titer compared to the saline-treated control mice, indicating that CMV infection is less severe in CSF-1-treated mice.

In a second experiment, 209 Balb/C mice (5 per group) were infected with a sublethal dose of mCMV ($2\times10^4$ pfu/mouse, i.p.) four hrs after the last CSF-1 dosing. CSF-1 was administered, i.p., once a day for 4 days at 4 dose levels (3.6, 0.9, 0.23 and 0.06 mg/kg/day). In this subacute infection model, mice were assessed for severity of infection by assaying vital titers (plague forming units on mouse embryo cells) in blood and organs (spleen, liver and kidney) at 7 days after infection. CSF-1-pretreated mice showed 75–97% reduction in viral titers in spleens, kidneys and livers as compared to saline treated control (P<0.01). The CSF-1 effect is dose dependent; mean spleen viral titer reduction of 97.4, 94.1 77.6 and 74.9% at CSF-1 dose levels of 3.6, 0.9, 0.23 and 0.06 mg/kg/day, respectively were observed as shown in the following table:

CMV, in which organ titers were monitored). When 50 ug/0.05 ml CSF-1 was administered intraperitoneally to 3.5–14.5 g Balb/C mice at day −1 or day −1, 0, 1, 2 and 3 (single dose given per mouse) before viral challenge ($4\times10^5$ pfu/mouse, 0.2 ml i.p.), after seven days there was a significant increase in survival, shown in the following table, as compared to saline-treated control.

| Group | Percent Survival |
|---|---|
| Controls | 3/10 |
| CSF-1 day-1 | 8/10 |
| CSF-1 days-1, 0, 1, 2, 3 | 7/10 |

Figure 5:
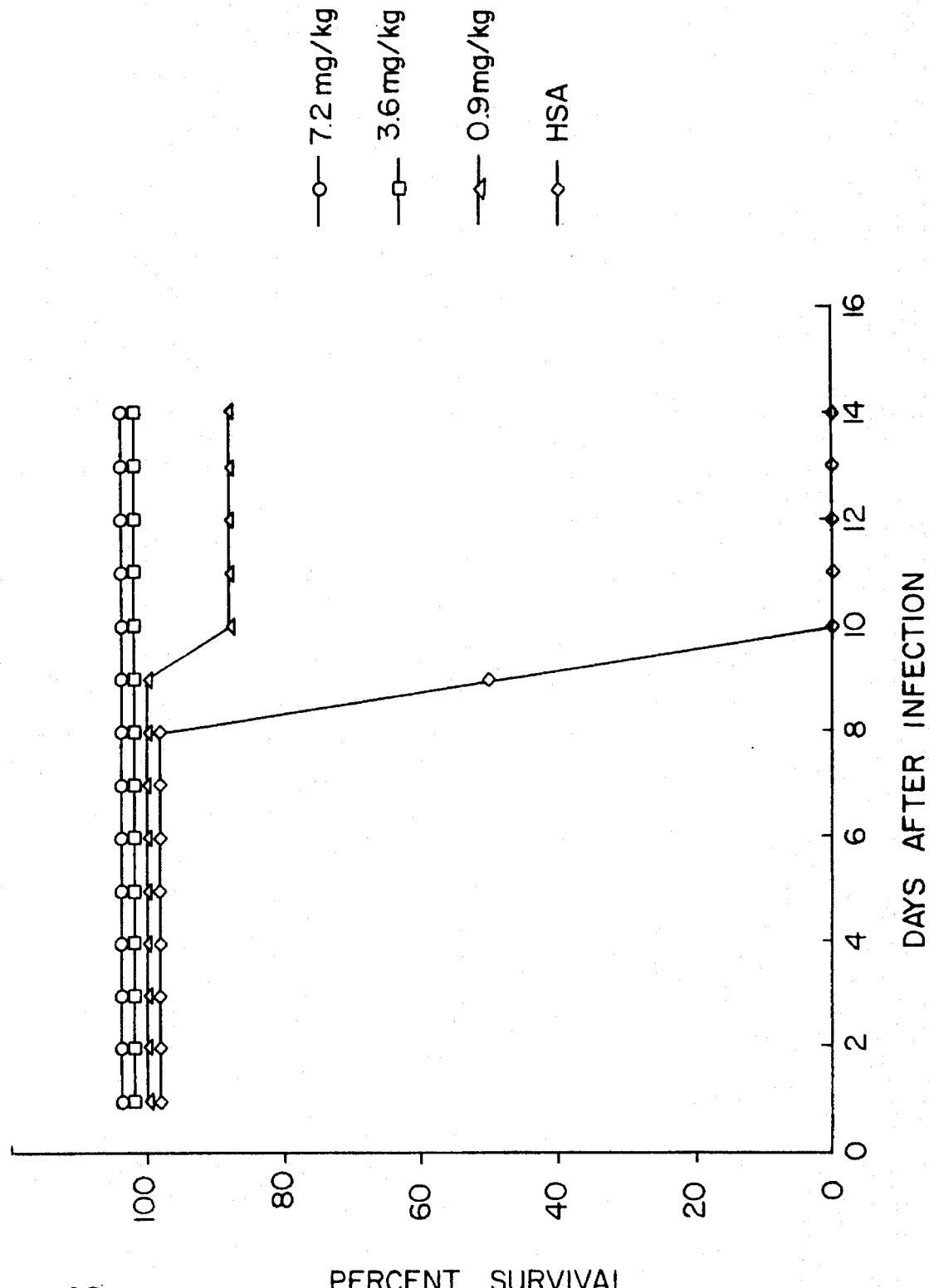
FIG. 5 shows a protective effect of CSF-1 against a lethal dose of murine cytomegalovirus (mCMV).

For prophylatic effect in the acute infection model, 13–14 g Balb/C mice were infected with a lethal dose of mCMV ($5\times10^4$ to $2\times10^5$ pfu/mouse, i.p.) four hrs after the last CSF-1 dosing (using the dose levels between 0.9 mg/kg/dayup to 7.2 mg/kg/day) and survival monitored for 14 days. In this acute infection model, CSF-1 significantly enhanced survival in mice challenged with mCMV at 50,000 pfu/mouse as shown in FIG. 5, although lower doses of CSF-1 (0.9 mg/kg and 3.6 mg/kg) appeared to be less effective in mice challenged with mCMV at 100,000 pfu/mouse.

These data demonstrate that CSF-1 can be used as an immunoprophylaxis for vital infection in clinical medicine. CSF-1 may be used alone or in combination with another lymphokine or antiviral agent in the treatment of viral infections in general, and in particular, may be beneficial in immunosuppressive viral infections such as acquired immune deficiency syndrome (AIDS).

The preferred dosage range administered i.p. is about 0.05–8.0 mg/kg CSF-1 per mouse per day.

In Vivo Prophylactic Treatment of Bacterial Infection with CSF-1

Outbred CD-1 mice were individually administered CSF-1, produced from the CV-1 cell line (short clone 158), one dose (10 ug/dose), administered- intraperitoneally one day before challenge with a lethal dose ($LD_{100}=6\times10^7$ cfu) of a clinical isolate of E. coli (SM18), a bacterium responsible for causing Gram-negative sepsis upon introduction into a host. The mice were then monitored for survival for 7 days

| | Dose Response of CSF-1 Effect on mCMV Organ Titer | | |
|---|---|---|---|
| | | Mean Viral Titer (% Decrease)[a] | |
| CSF-1 Dose (mg/kg/day) | SPLEEN $\times 10^4$ pfu/g | LIVER $\times 10^2$ pfu/g | KIDNEY $\times 10^2$ pfu/g |
| 3.6 | 16.0 ± 2.1 (97.8)[b] | 17.5 ± 2.5 (92.1)[b] | 2.5 ± 2.5 (95.7)[b] |
| 0.9 | 32.9 ± 6.4 (95.3)[b] | 35.0 ± 10.0 (84.3)[b] | 17.5 ± 2.5 (69.6)[b] |
| 0.23 | 135.0 ± 25.0 (80.9)[c] | 97.5 ± 12.5 (56.2)[c] | 7.5 ± 7.5 (87.0)[c] |
| 0.06 | 260.0 ± 25.0 (63.1) | 90.0 ± 5.0 (59.6)[b] | 2.5 ± 0 (56.5) |
| HSA saline | 705.0 ± 41.7 | 222.5 ± 47.5 | 57.5 ± 12.5 | a = Data represent mean organ titer from five animals assayed individually. Value in parenthesis refers to percent decrease in organ titer as compared to HSA saline control.
b = p < 0.01
c = p < 0.05

Separately, CSF-1 produced in E. coli (NV3CV221) has been tested in a lethal mCMV infection model (this is in contrast to the above experiment using sublethal doses of post-infection. The data show that pretreatment with CSF-1 enhanced the survival of mice challenged with lethal doses of E. coli.

This experiment was also conducted using the LCSF NV3CV221 bacterially produced CSF-1. Each lot of CSF-1 was tested in 4-fold dilutions for a total dose range of $1\times10^7$ to $1.7\times10^8$ units/kg body weight. Minimum protective dose was defined as single daily dose (administered once a day for 5 days, i.p.) before i.p. infection with *E. coli* ($6 \times 10^7$ cfu/mouse) which produced statistically significant (p value less than 0.05 Fisher's Exact test) enhancement of the survival of treated mice as compared to saline or boiled CSF-1 control mice.

| Group | Dose | Percent Survival[a] |
|---|---|---|
| Saline | — | 0 |
| CSF-1 | 2.97 mg/kg | 100 |
| CSF-1 | 0.74 mg/kg | 90 |
| CSF-1 | 0.18 mg/kg | 10 |
| Boiled[b] CSF-1 | 2.97 mg/kg | 0 |
| Boiled CSF-1 | 0.74 mg/kg | 20 |
| Boiled CSF-1 | 0.18 mg/kg | 0 |

[a]Data represent percent of animals surviving at day 7 after infection
[b]Heat inactivated controls Experiments were conducted to study the effect of dose scheduling on the induction of CSF-1 effects on host resistance. Groups of mice (10) were administered CSF-1 at 0.9 mg/kg/dose per day for either 1, 2, 3, 4 or 5 days. Mice were then challenged with *E. coli* ($6\times10^7$ cfu/mouse) i.p. 4 hrs after the last CSF-1 injection.

To induce a protective effect the data show that multiple doses of CSF-1 starting between 52 and 100 hours before bacterial infection is effective.

| CSF-1[a] Dose Schedule | Time Before[b] Infection | Percent Survival[c] Day 7 | p[d] Value |
|---|---|---|---|
| QD × 1 | 4 | 10 | |
| QD × 2 | 28 | 10 | |
| QD × 3 | 52 | 60 | <0.05 |
| QD × 4 | 76 | 90 | <0.01 |
| QD × 5 | 100 | 100 | <0.01 |
| Saline | 76 | 0 | |

[a] = Groups of 10 mice were treated with CSF-1, i.p. (at 0.9 mg/kg/dose/day, for one, two, three, four or five days (i.e. QD × 1 to QD × 5) before *E. coli* infection at four hours after the last CSF-1 dose.
[b] = Duration in hours between the first dose of CSF-1 and the time of infection with *E. coli*.
[c] = Data represent percent of animal surviving at 7 days after infection.
[d] = By Fisher's Exact test, as compared with the saline control group.

Single bolus injection (0.2 to 9.0 mg/kg) at either 4, 18, 28, 52 or 76 hrs before infection was not effective at inducing enhanced host resistance.

The data show that pretreatment with CSF-1 significantly enhances survival of mice challenged with lethal doses of *E. coli*. The effect is dependent, however, on the dose of CSF-1, the timing, and the schedule of administration. At the higher doses of approximately 0.7 to 3.0 mg/kg/day, nearly complete protection was seen. At the lower dose of 0.2 mg/kg, there was also protection but the effect was smaller.

Leukopenic Infection Model

Results of CSF-1 induced protection in *E. coli* infection in mice pretreated with 50 mg/kg cyclophosphamide (CY). The $LD_{50}$ of CY for mice is at about 400 mg/kg, the lower CY dose we used represents ⅛ of the $LD_{50}$. This dose, when injected i.p. 3 days earlier, induced a decrease in total white blood cells and neutrophils, and rendered mice more susceptible to *E. coli* infection (e.g., infection with $3\times10^7$ cfu/mouse killed 100% of CY treated mice but only 20% of mice not given this dose of CY). When CSF-1 was given to CY treated mice (CSF-1 at 0.89 mg/kg, once/day for 4 days, i.p.), there was 100% survival as compared to 30% in mice given saline instead.

In Vivo Effect of CSF-1 on *Candida albicans*

CSF-1 was administered to outbred CD1 mice (27–28g, females) as daily i.p. doses for 3 to 4 days before challenge with a lethal dose of *C. albicans* ($1.5\times10^8$ yeast cells/mouse, i.p.). This challenge dose resulted in a median survival time (MST) of 3.0 days in non-treated and saline treated mice. CSF-1 treated mice showed MST of 15 and 13 days at doses of 1.9 and 0.1 mg/kg, respectively. This 4-fold enhancement in survival time is significant at p=0.01 (Log Range Tests). To minimize any possible interference from endotoxin, highly purified CSF-1 was used which is virtually free of endotoxin (<0.05 ng/mg protein). It was also showed that the prophylatic effect was abrogated by heat-inactivation of CSF-1 test material. This protection was associated with increased numbers of peripheral blood circulating monocytes and neutrophils and a 2- to 3-fold increase in peritoneal macrophages. We conclude that CSF-1 enhanced host resistance against *C. albicans* infection and that this effect is probably mediated by activation of macrophages and neutrophils.

CSF-1 was also tested in an additional model in which *C. albicans* was delivered systemically (i.v.). CSF-1 at a dose of 1.9 mg/kg/day QD×4 was administered either i.p. or i.v. $2\times10^5$ cfu/mouse were injected i.v. 4 hours after the last dose of CSF-1. Either of these administrations resulted in a significant enhancement of survival when compared to saline injected control mice.

Adjunctive In Vivo Effect of CSF-1 on Fungal Infections

Four patients were treated with 2 hour daily intravenous infusion of CSF-1 at doses of 100 ug/m² to 200 ug/m² for periods of 7 to 21 days. Each of these patients have had systemic fungal infections caused by *Candida* species as observed by lung or liver involvement or by positive blood culture. Three patients (male) were treated adjunctively with amphotericin-B (up to 1.0 mg/kg/day i.v.) post-allogenic bone marrow transplant—one of these had infection documented prior to transplant, the other two apparently acquired infection post transplant. These three patients died of complications of bone marrow transplantation. One, who died shortly after the initiation of CSF-1 therapy could not be assessed, the other two had no evidence of fungal infection at autopsy.

The fourth patient (female) developed severe *Candida* infection post autologous bone marrow transplant. This patient was unable to tolerate amphotericin-B and required dialysis and intubation. This patient had multiple *Candida* pulmonary nodules on CAT scan. Within a week on CSF-1 and Diflucan (fluconazole - Pfizer) supportive therapy, she was ambulatory and left the hospital. The patient's pulmonary lesions resolved as did the need for dialysis. This patient continues to be followed.

In Vivo Stimulation of White Blood Cell Count

Outbred CD-1 mice were administered purified recombinant human CSF-1, at 2 mg/kg per dose, three times a day for five consecutive days. Total white blood cell count increased to 12,000–13,000/ul in CSF-1-treated mice from 8,700/ul in saline-treated control mice. In addition, neutrophil count increased to 6,821/ul in CSF-1-treated mice as compared to 1,078/ul in saline-treated control mice.

This effect is dependent on the dose of CSF-1 and the schedule of administration. The increase in peripheral blood neutrophils was detectable 2–4 hours after a single dose of CSF-1 was administered intraperitoneally. These results indicate that CSF-1 administration may be useful in clinical or veterinary medicine as a stimulus of granulocyte production and an enhancer of white blood count.

CSF-1 in Wound Healing

CSF-1 is assayed for wound healing using animal models and protocols such as the Gorerex miniature wound healing model of Goodson and Hunt (*J Surg Res* (1982) 33:394). in which implanted Gorerex tubes fill up with invading macrophages, fibroblasts and other connective tissue cells, and collagen and fibrin deposition. Healing is assessed by examining tube contents microscopically. A second model is the excisional wound healing model of Eisenger et al (*Proc Natl Acad Sci, USA* (1988) 85:1937) in which wounds are observed visually and punch biopsies are taken to monitor healing, density of cells, and number of epidermal cell layers arising from hair follicles. A third model is a serosal model such as the heat-injured testicular serosa of Fotev et al (*J Pathol* (1987) 151:209) in which healing is assessed in fixed sections by degree of mesothelial resurfacing of the injured site. The teachings of each of these models are incorporated herein by reference.

Generally, CSF-1 is applied to the site of the wound by soaking a nonadhesive surgical dressing in $10^4$ to $10^8$ U/ml of CSF-1 in saline as described in the excisional wound healing model reference using epidermal cell derived factor (EGF) for topical wounds. Alternatively, similar amounts of CSF-1 are introduced into Gorerex tubes at the time of implantation as described in Goodson and Hunt, supra, or CSF-1 may also be incorporated into a slow-release matrix and applied at the site of the wound (in Goretex tubes, in or under dressings, in a slow release gelatin or collagen-based matrix or by injection in the peritoneal cavity) by systemic treatment 1–3 times a day (i.v., i.p., or s.c.) at a dose of 10 to 10,000 ug/kg/day.

In a full thickness dermal excisional model, experimental groups of five female BDF-1 mice, weighing 18 to 20 grams, were anesthetized by methoxyflurane inhalation (Metofane, Pitman-Moore, Inc., Washington Crossing, N.J.). Wounds were made using a clean surgical technique. Hair on the dorsum and sides was clipped, and the skin swabbed with 70% ethanol and dried. A strip of transparent tape was applied over the back, approximately midway between the sacrum and scapulae. The skin was elevated parallel to the length of the mouse, and full thickness excisional wounds were created using a 6 mm diameter punch. The tape was removed, exposing an 8 to 10 mm wide strip of intact skin between the left and right circular bilateral wounds. Triple antibiotic ointment (polymyxin B-bacitracin-neomycin) was applied to the fresh wound using a cotton tipped swab stick.

Wounds were measured with hand held calipers in their anterior-posterior and transverse dimensions on days 0, 1, 2, 3, 4, 5, 7, 9 and 10 (with day 0 representing the day of wounding). Although the wounds were circular initially, they tended to heal in a elliptical shape. For this reason, approximate wound area was calculated using the formula for the area of an ellipse A=pi(BxC)/4, where A=area (mm2), B=wound diameter (mm) of the anterior-posterior axis, and C=wound diameter (mm) of the transverse axis. Percent wound closure was calculated for each wound by dividing the area at any given time point by initial wound area on day 0.

*E. coli* produced long clone CSF-1 N$\nabla$3C$\nabla$7221 (specific activity $>6.0 \times 10^7$ units/mg) was diluted in 0.9% sodium chloride, USP, and delivered intravenously via the lateral tail vein in a final injection volume of 100 ul. Doses of CSF-1 ranging from 0.5 mg/kg/day (10 ug/day) to 10.0 mg/kg/day (200 ug/day) were administered daily for a total of 7 days, with the first dose occurring approximately 4 hours after wounding. Human serum albumin (HSA) diluted in 0.9% NaCl was chosen as a non-specific protein control, and was administered to control animals at a dose of 5.0 mg/kg/day.

Statistical analysis was done by individual Student t test comparisons between treatment groups on each day. For all comparisons, statistical significance was noted when $p<0.05$.

Little or no hemorrhage occured in fresh wounds. A thin fibrinous covering was evident over wounds within 12–24 hours, progressing to a scab within 1–2 days. The scabs contracted as they dried, gradually becoming less adherent to the underlying granulation tissue, but did not distort the wound area measurements. Mean wound area was calculated from measurements of the right and left wounds of 5 mice for each group and day. Initial wound area did not differ among any of the treatment groups.

Figure 6:
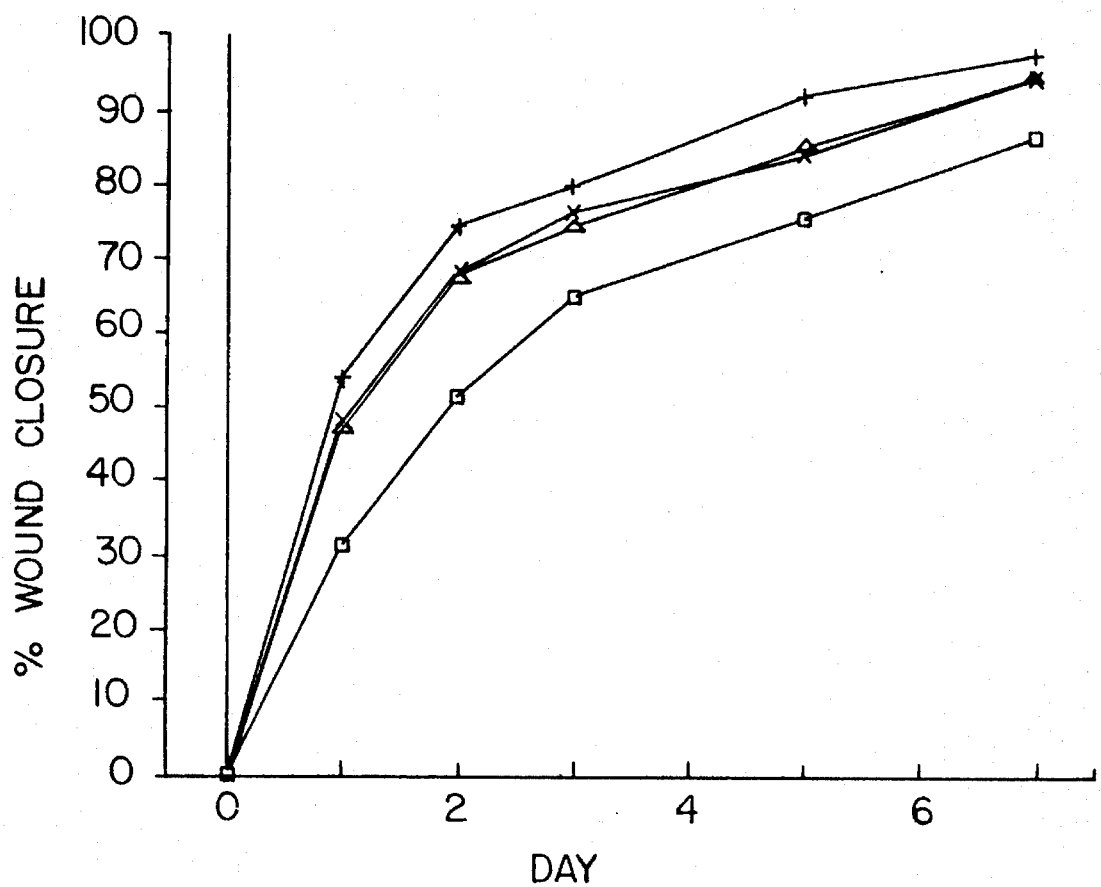
FIG. 6 shows wound closure data in control and CSF-1 treated mice.

As shown in FIG. 6, wound closure was more rapid in CSF-1 treated mice than in HSA treated controls, where closure was defined as the percent reduction in initial wound area on a given day. The values provided in FIG. 6 represent the means of five mice at each timepoint. CSF-1 treated group differed from the controls at all timepoints ($p<0.05$). The "square" represents the control; the "+" represents CSF-1 (10.0 mg/kg/day); the "triangle" represents CSF-1 (5.0 mg/kg/day); and the "×" represents CSF-1 (0.5 mg/kg/day). The greatest enhancement in wound closure was observed in mice receiving 10.0 mg/kg/day. Intermediate (5.0 mg/kg/day) and low (0.5 mg/kg/day) doses of CSF-1 also significantly increased rates of wound closure, while at these two doses the response was nearly equivalent.

The enhanced rate of wound closure seen in CSF-1 treated wounds appeared to result from a more rapid initial phase which occurred within the first few days. During this period, closure was enhanced approximately 40% by CSF-1 as shown in the following table. Thereafter, the rate of closure in all groups was nearly identical and began to decline steadily until the wounds were completely healed. Wounds of CSF-1 treated mice reached 50% closure 1 to 2 days sooner than HSA treated controls (FIG. 6), yet the period of time required for wounds to reach 100% closure was approximately 10 days for all groups.

|  | Control | | | *CSF-1 | | | | |
| --- | --- | --- | --- | --- | --- | --- | --- | --- |
| Days post-wound | Wound area (mm2) | Standard Deviation (mm2) | Wound closure (%) | Wound area (mm2) | Standard Deviation (mm2) | Wound closure (%) | Enhanced[a] closure (%) | P value relative to control |
| 0 | 35.2 | 7.5 | 0.0 | 34.4 | 8.1 | 0.0 | — | 0.828 |
| 1 | 25.2 | 6.9 | 28.4 | 18.4 | 3.6 | 46.6 | 39.0 | 0.017 |
| 2 | 19.4 | 4.8 | 44.7 | 11.6 | 2.3 | 66.1 | 32.4 | 0.000 |
| 3 | 17.4 | 5.2 | 50.5 | 9.0 | 2.4 | 73.9 | 31.7 | 0.000 |
| 4 | 11.2 | 3.7 | 68.1 | 7.8 | 2.6 | 77.2 | 11.8 | 0.037 |
| 5 | 9.9 | 3.1 | 71.8 | 5.1 | 1.9 | 85.2 | 15.7 | 0.001 |
| 7 | 5.0 | 3.1 | 85.7 | 2.6 | 1.0 | 92.4 | 7.3 | 0.045 |
| 10 | 0.0 | 0.0 | 100.0 | 0.0 | 0.0 | 100.0 | 0.0 | — |

*CSF-1 was administered to mice intravenously at a dose of 5.0 mg/kg/day for a total of 7 days, beginning 4 hours after wounding

[a]Enhanced closure calculated as: $\frac{\% \text{ closure (control)} - \% \text{ closure (treated)}}{\% \text{ closure (control)}}$ Gross observations made at time points from day 3 to day 10 suggested that changes in the vascular content of the skin surrounding the wound space occurred during the course of healing in control and CSF-1 treated wounds. As early as 3 days post-wounding, increased vasculature (larger and more tortuous vessels) was evident by the naked eye in regions of skin surrounding the wound sites in control mice. By day 7, the vascular content of skin surrounding control wounds had decreased while the skin surrounding the wounds in CSF-1 treated mice showed significantly greater vascularization than did the control mice, both in areas around the wound and in vessels not adjacent to the site of wounding. This response appeared to include both a greater number of vessels and more extensive branching.

CSF-1 may also be used in combination with other growth factors to promote wound healing such as epidermal growth factor (EGF), fibroblast growth factor (basic and acidic FGF), platelet derived growth factor (PDGF) or transforming growth factors (TGF alpha and beta), IL-1, IL-2, platelet derived wound healing factor (PDWHF) and other substances such as somatomedin C and vitamin C.

Formulation and Dosage of CSF-1

The recombinantly produced human CSF-1 may be formulated for administration using standard pharmaceutical procedures. Depending on ultimate indication, CSF-1 will be prepared in an injectable or a topical form, and may be used either as the sole active ingredient, or in combination with other proteins or other compounds having complementary or similar activity. Such other compounds may include alternate antitumor, e.g., chemotherapeutic agents such as adriamycin, or lymphokines, such as IL-1, -2, -3, -4, and -6, alpha-, beta-, and gamma-interferons, CSF-GM and CSF-G, and tumor necrosis factor. The effect of the CSF-1 active ingredient may be augmented or improved by the presence of such additional components. As described above, the CSF-1 may interact in beneficial ways with appropriate blood cells, and the compositions of the invention therefore include incubation mixtures of such cells with CSF-1, optionally in the presence of additional lymphokines or cytokines. Either the supernatant fractions of such incubation mixtures, or the entire mixture containing the cells as well, may be used. Staggered timing may be preferred for some combinations, such as CSF-1 followed one to two days later by gamma interferon.

The CSF-1 described herein is generally administered therapeutically in amounts of between 0.01–10 mg/kg per day, whether single bolus administration or fractionated over 24 hr, for all indications, e.g., treatment of infectious disease, wound healing, restoration of myleopoiesis and immunity, and cancer.

The scope of the invention is not to be construed as limited by the illustrative embodiments set forth herein, but is to be determined in accordance with the appended claims.

We claim:

1. A method for therapeutic treatment of a bacterial infectious disease in a mammal which comprises administering to said mammal an effective amount of recombinant colony stimulating factor-1 (CSF-1).

2. The method of claim 1 wherein the bacterial infectious disease is Gram-negative sepsis.

3. The method of claim 1 wherein the recombinant CSF-1 is administered in conjunction with an efficacious antimicrobial agent, cytokine, or lymphokine.

4. A method for treating a bacterial infection comprising administering an effective amount of colony stimulating factor-1 to a mammal in need thereof.

* * * * *